(12) United States Patent
Carter et al.

(10) Patent No.: US 7,208,580 B2
(45) Date of Patent: Apr. 24, 2007

(54) ATOMIC STRUCTURE OF THE HEMALBUMIN COMPLEX AND ITS USE IN DESIGNING THERAPEUTIC COMPOUNDS

(75) Inventors: Daniel C. Carter, Huntsville, AL (US); Joseph Ho, Madison, AL (US); Zhong Min Wang, Madison, AL (US)

(73) Assignee: New Century Pharmaceuticals, Inc., Huntsville, AL (US)

( * ) Notice: Subject to any disclaimer, the term of this patent is extended or adjusted under 35 U.S.C. 154(b) by 0 days.

(21) Appl. No.: 10/506,043

(22) PCT Filed: Mar. 3, 2003

(86) PCT No.: PCT/US03/06331

§ 371 (c)(1),
(2), (4) Date: Apr. 6, 2005

(87) PCT Pub. No.: WO03/074128

PCT Pub. Date: Sep. 12, 2003

(65) Prior Publication Data

US 2005/0182246 A1    Aug. 18, 2005

Related U.S. Application Data

(60) Provisional application No. 60/361,074, filed on Mar. 1, 2002.

(51) Int. Cl.
*C07K 14/76* (2006.01)
*C07K 14/795* (2006.01)
*G01N 23/207* (2006.01)

(52) U.S. Cl. ............... 530/362; 530/363; 540/145; 540/201; 378/73

(58) Field of Classification Search ............ 530/362, 530/363; 435/7.7; 540/145, 201; 378/73
See application file for complete search history.

(56) References Cited

U.S. PATENT DOCUMENTS 5,780,594 A * 7/1998 Carter .................. 530/363
5,948,609 A * 9/1999 Carter et al. ............ 435/1.2

OTHER PUBLICATIONS

Wardell, Mark, Biochem. Biophys. Res. Commun. 291(4), 813-819, 2002.*
Carter, Eur. J. Biochem 226, 1049, 1994.*
Komatsu, J Am Chem Soc 126, 14304, 2004.*

* cited by examiner

*Primary Examiner*—David Lukton
(74) *Attorney, Agent, or Firm*—B. Aaron Schulman; Stites & Harbison PLLC

(57) ABSTRACT

A high resolution structure of the hemalbumin binding complex is provided which includes the detailed atomic coordinates which reflect the binding site and the binding characteristics of the structure. This high resolution structure can be used in methods of determining the primary residues involved in gas binding, redox potential of iron, etc., and thus will be used to identify and optimize the gas binding characteristics of heme and albumin, so as to allow for the development of modified recombinant albumins containing heme and/or heme derivatives which have improved gas binding properties and which can be used for therapeutic purposes.

3 Claims, 3 Drawing Sheets

ATOMIC STRUCTURE OF THE HEMALBUMIN COMPLEX AND ITS USE IN DESIGNING THERAPEUTIC COMPOUNDS

CROSS-REFERENCE TO RELATED APPLICATIONS

This application claims the benefit of U.S. Provisional Application Ser. No. 60/361,074, filed Mar. 1, 2002.

FIELD OF THE INVENTION

This invention relates in general to a high resolution crystal structure of hemalbumin, and in particular to the atomic coordinates for the binding region between serum albumin and heme, methods of obtaining those coordinates, and methods of using said coordinates to obtain vital information regarding potential binding sites in albumin and heme so as to enable the development of genetically modified versions of these molecules with improved binding properties and therapeutic usefulness.

BACKGROUND OF THE INVENTION

The serum albumins are the major soluble proteins of the circulatory system and contribute to many vital physiological processes. Serum albumin generally comprises about 50% of the total blood component by dry weight, and as such is responsible for roughly 80% of the maintenance of colloid osmotic blood pressure and is chiefly responsible for controlling the physiological pH of blood. The albumins also play an extremely important role in the transport, distribution and metabolism of many endogenous and exogenous ligands in the human body, including a variety of chemically diverse molecules including fatty acids, amino acids, steroids, calcium, metals such as copper and zinc, and various pharmaceutical agents. The albumins are generally thought to facilitate transfer many of these ligands across organ-circulatory interfaces such as the liver, intestines, kidneys and the brain, and studies have suggested the existence of an albumin cell surface receptor. See, e.g., Schnitzer et al., P.N.A.S. 85:6773 (1988). The albumins are thus intimately involved in a wide range of circulatory and metabolic functions.

Human serum albumin (HSA) is a protein of about 66,500 kD protein and is comprised of 585 amino acids including at least 17 disulfide bridges. As with many of the albumins, human serum albumin plays an extremely important role in human physiology and is located in virtually every human tissue and bodily secretion. As indicated above, HSA has an outstanding ability to bind and transport and immense spectrum of ligands throughout the circulatory system including the long-chain fatty acids which are otherwise insoluble in circulating plasma. Certain details regarding the atomic structure and the binding affinities of albumin and the specific regions primarily responsible for those binding properties have previously been disclosed, e.g., in U.S. patent application Ser. No. 08/448,196, filed May 25, 1993, now U.S. Pat. No. 5,780,594 and U.S. patent application Ser. No. 08/984,176, filed Dec. 3, 1997, now U.S. Pat. No. 5,948,609, both of which are incorporated herein by reference.

Because of the vital role played by albumins, there are literally thousands of applications for serum albumin covering a wide range of physiological conditions. However, unlike blood proteins such as hemoglobin, native serum albumins are non-functional as oxygen transport systems, and thus have not been useful in blood replacement systems requiring oxygen transport. Accordingly, one recent focus of research has been the binding of the albumin molecule with heme, one of the important blood proteins. Under normal physiological conditions, heme that finds its way into plasma is bound by the specific heme-binding protein, hemopexin, which delivers it to the liver for excretion via a receptor-mediated uptake mechanism (1–5). Under pathophysiological conditions of severe hemolysis when significant amounts of free hemoglobin appear in the circulation, serum albumin can also become a significant transporter of heme (6,7), principally as hemin ($Fe^{III}$ Protoporphyrin-IX (Cl)). These are conditions when hemopexin becomes saturated by hemin, and albumin, which is present at considerably higher concentration than hemopexin, acts as a depot for the overflow. Additionally, a source of heme uptake by albumin has been suggested to result from the uptake of soluble heme-containing peptides released by the enzymatic digestion of dietary heme-containing proteins such as cytochrome c, where they may constitute a significant route by which iron enters the mammalian system (8).

Hemin is one of the important endogenous ligands transported and/or sequestered by human albumin and among the most highly bound having with a predicted a single high affinity site with $K_A=1.1 \times 10^8$ $M^{-1}$ (9). Interestingly, among mammals, only albumin of primates shows a single high affinity heme binding site (4). Studies of heme binding to albumin suggest a two step binding process, a fast interaction to form an intermediate complex, followed by "internalization" of the hemin in a region with limited access to bulk aqueous solvent (9,10). Although various hypotheses concerning the binding location and chemistry to human albumin have been proposed from spectroscopic and other methods (11–17), except for the general binding location within cleavage fragments (IB-IIA) (6) and more recently recombinant domains (domain I) (18), the conclusions of all of the other studies are inconsistent with the location and coordination of the atomic structure of the complex in accordance with this invention as described herein.

Previously, the structure of human methemalbumin was determined at 2.8 Å (19) using a crystal form of the space group C2, i.e. form-III as reported in reference (20). These publications evidenced that the heme binds to albumin within the IB pocket, a site that was previously identified with long chain fatty acid transport. In addition, a successful blood replacement product was obtained which featured a heme-albumin complex with a recombinant serum albumin having at least one of the four key hydrophobic binding residues in the heme binding region replaced with a histidine, such as disclosed in U.S. Pat. No. 5,948,609, incorporated herein by reference. However, the ability to uncover additional information which would lead to further breakthroughs with regard to the capacity of albumin to be utilized to further improve gas binding properties has heretofore been limited by the resolution of the crystal albumin structure obtainable. Similarly, it is also important to obtain additional insights with regard to the heme molecule and its derivatives so as to be able to develop heme molecules and derivatives which when combined with albumin will provide oxygen or other gas binding/transport delivery properties or allow for other applications such as scavenging of toxic gases (e.g., cyanide, nitric acid, carbon monoxide, etc.).

Accordingly, it is highly desirable to develop a system of determining key binding regions of the heme/albumin complex and to develop a means by which the alteration of albumin or heme genetically can be accomplished so as to identify and maximize the medically relevant gas binding properties of these molecules, a goal that has not previously been achievable with lower resolution pictures of the albumin crystal complex structure at the relevant gas binding sites.

SUMMARY OF THE INVENTION

Accordingly, it is thus an object of the present invention to provide a higher resolution picture of albumin at the hemalbumin binding complex so as to be useful in determining novel sites which will be used to identify and maximize albumin gas binding characteristics.

It is further an object of the present invention to provide a method for developing high resolution atomic coordinates of the heme/albumin complex that will allow the design of therapeutics based on the complex and allow for the development of modified recombinant albumins which have improved gas binding properties.

It is further an object of the present invention to provide a method for guiding the development of novel small molecule heme derivatives which when combined with albumin will have maximized gas-binding properties so as to be useful in a wide variety of applications including delivery of oxygen, binding, transport or delivery of other gases, and scavenging of potentially toxic gases (e.g., cyanide, nitric acid, carbon monoxide, etc.).

It is still further an object of the present invention to provide high resolution atomic coordinates of the heme/albumin complex that will allow the design of therapeutics based on the complex and allow for the development of modified recombinant albumins which have improved gas binding properties.

These and other objects of the present application are obtained by virtue of the present invention which comprises a method of obtaining high resolution atomic coordinates of the heme/albumin complex, and which provides the atomic coordinates thereof in a manner not previously possible. The provision of the high resolution atomic coordinates of this crystal complex in accordance with the invention allows for the identification of key binding sites and will thus allow for the development of genetically modified albumin and heme molecules which have maximized gas binding properties and which can be useful in many applications such as binding, transport, and delivery or therapeutic gases such as oxygen, and scavenging and removal of potentially toxic gases such as cyanide, nitric acid, carbon monoxide, etc.

BRIEF DESCRIPTION OF THE DRAWINGS

The present invention is further illustrated in the drawings, wherein.

DETAILED DESCRIPTION OF THE PREFERRED EMBODIMENTS

Figure 1:
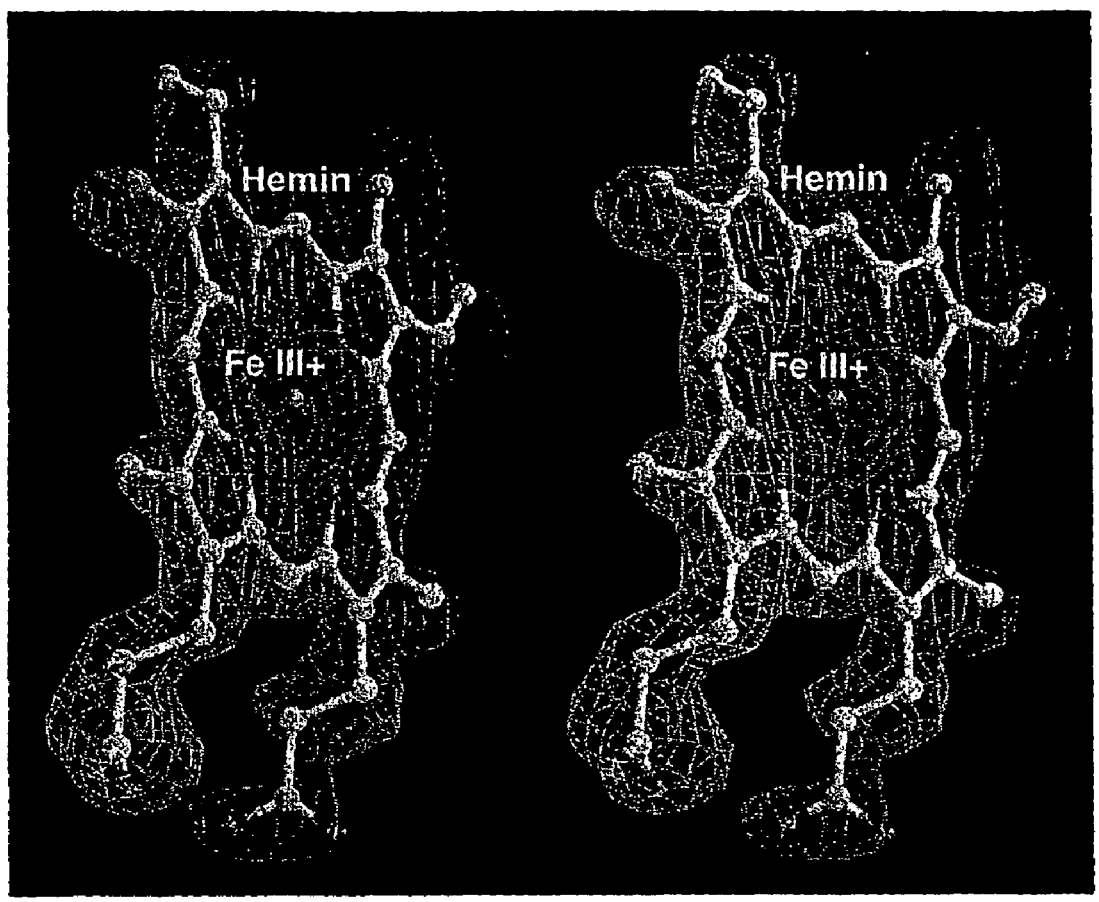
FIG. 1 is a stereo view illustrating the difference density for the hemin ($F_{obs}-F_{calc}$) shown contoured at $3\sigma$ after a simulated annealing refinement without the incorporation of heme into the model. The heme coordinates from the final refined structure are shown superimposed on the initial difference density. The protrusion of the Fe electron density toward the proximal side indicating a position above the heme plane in the direction of Tyr-161, can be clearly seen.

In accordance with the present invention, there are provided atomic coordinates for the heme/albumin binding complex (or "hemalbumin") which is obtained as a high resolution structure as determined by single crystal X-ray diffraction to a resolution of 1.9 Angstroms. As described further below, The structure as determined in the present invention revealed that protoporphyrin IX was bound to a single site within a hydrophobic cavity in subdomain IB, one of the principal binding sites for long chain fatty acid. This iron is penta coordinated with the fifth ligand comprised of the hydroxyloxygen of Tyr-161 (phenolic oxygen to heme plane distance: 2.73 Å) in an otherwise completely hydrophobic pocket. The heme propionic acid residues form salt bridges with His-142 and Lys-190, which together with a series of hydrophobic interactions, enclose and secure the hem within the IB helical motif. A detailed description of the structure together with its implications for the development of potential blood substitutes is provided hereinbelow.

As explained further in U.S. Pat. No. 5,948,609, the initial complex of heme and albumin subject to the high resolution of the present invention may be obtained in a number of suitable ways, such as by dissolving hemin and combining it with serum albumin such as a natural or recombinant serum albumin such as described above. As will be set forth below, the albumin used may be one in its unmodified state so as to determine the precise nature of the key residues involved in heme/albumin binding. Further, in accordance with the invention, hemin may be combined with a serum albumin that has been modified at certain key residues so as to enhance gas binding properties, and the high resolution of such structures in accordance with the invention can assist in determining if such modifications result in improved binding complexes. Heme, or protoporphyrin, is one of the many metabolic products of endogenous origin and is produced from myoglobin and hemoglobin. In general, it appears that only the albumins from primates have a specialized high affinity site for protoporphyrin, and binding constants for this ligands are on the order of $1 \times 10^8$ Ka. In accordance with the invention, crystals of human serum albumin have been complexed with heme and studied using high resolution crystallographic means which have provided the atomic coordinates needed to investigate atomic interactions between albumin and heme and use the information to better model these molecules for maximization of binding properties.

In order to utilize crystallographic processes to study the binding between heme and albumin, hemin was dissolved and combined with human serum albumin in a 1:1 Molar ratio, which produces methemalbumin which is also crystallized utilizing conditions such as those disclosed in Carter et al., 1994 and co-pending U.S. patent application Ser. No.

08/448,196, incorporated herein by reference. X-ray diffraction data were collected and subsequent printouts produced from these data provides precise information concerning the binding location and chemistry of the heme/albumin complex.

In the particularly preferred embodiment, the hemalbumin crystals may be prepared in a manner previously described (19,20). The human albumin is defatted in the manner described in Chen (21) and is preferably coupled with 1:1 molar ratio of albumin:hemin ($Fe^{III}$-Protoporphyrin-IX (Cl)) prior to coupling with myristate, although this is not always required. The crystals are of the same C2 form as the form-III of reference (19). Diffraction data were collected at the Beamline 5.0.3 of the Advanced Light Source (ALS), Lawrence Berkeley Laboratory (LBL). A 2×2 array (ADSC) of CCD detectors was used with a detector-to-crystal distance of 180 mm. A total of 180 (1°) oscillation images were collected from one crystal at 100 K using photon wavelength of 1.0 Å and exposure of 60 second per frame. At the cryogenic temperature, the unit cell dimensions were a=183.11 Å, b=37.91 Å, c=94.83 Å, $\beta$=105.04°. These images yielded a data set of 44,335 independent reflections with positive intensities to a resolution of 1.9 Å ($R_{merge}$: 3.7%; average multiplicity: 2.03; average $I/\sigma(I)$: 14.7, and completeness: 88.1%).

The program package of CNX X-ray from Accelrys, Inc. was used for structure refinement, with the protein starting model taken from a structure of human albumin complexed with myristate (without hemin) determined in our earlier studies (19,22) and re-refined more recently at 100 K. The hemin and five myristate molecules were clearly resolved in the difference density maps after initial refinement. When hemin, myristates, and solvent water molecules were incorporated in the model, the refinement quickly converged to an R-factor of 22.8% for all 42,107 reflections in the working set with no sigma cut-off (R-free 28.2%), yielding a structure of good geometry giving rms deviations from ideality of 0.005 Å for bond-distance and 1.19° for valence-angle. The final model includes 583 protein residues, 1 hemin molecule, 5 myristic acid molecules and 581 solvent water molecules with an average B-factor of 27.8 Å$^2$ for the protein atoms. One residue each at both N- and C-termini were not visible on the electron density maps, presumably disordered, and were not included in the model. Atomic coordinates of the methemalbumin structure at the binding region IB are included herein as Appendix A.

In accordance with the present invention, a hemalbumin structure was well determined and represents the highest resolution albumin structure reported to date, and details of the refinement statistics are provided in Table I included below. The quality of the resulting electron density is high providing detailed information of the heme binding interaction as well as other important structural information such as positions of key water molecules. The orientation of the heme ($Fe^{III}$-Protoporphyrin-IX) provides a good fit to the electron density as shown in FIG. 1. There is the possibility that a mixture of the two orientations actually exists in the complex (180 degree rotational isomers along the CHA to CHC line). However, the orientation chosen provides the best fit, and neither orientation affects the resulting interpretation of the binding chemistry. The overall structure of methemalbumin is very similar to the HSA-myristate structure as previously determined and used in this work to derive the phases for the methemalbumin structure (discussed above); and the structure using the same crystal forms and reported by others (23). The structures have an rms deviation between Cα atom of positions of 0.396 Å. When Cα for residues 109–195 that constitute the IB subdomain are superimposed, the rms was 0.32 Å.

Figure 2:
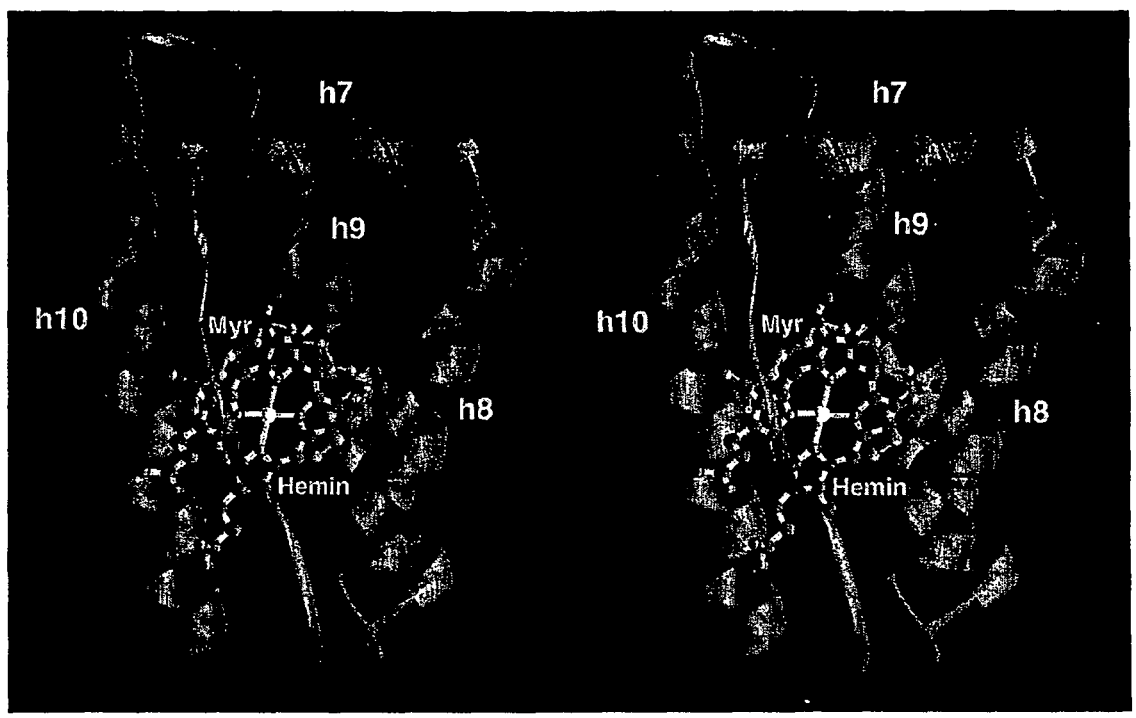
FIG. 2 is a stereo view of the $C_\alpha$ carbon tracing of subdomain IB (red) illustrating the helical motif (helices h7 through h10) and the binding location of the heme (green) in the binding pocket. Additionally, the striking overlap of the binding site with myristate (yellow) is shown for comparison.

A single site for hemin revealed by earlier lower resolution studies (19) was verified in accordance with the high resolution form of the present invention. The hemin is located within the IB subdomain which is constituted by a loop and four contiguous helices (h7, h8, h9 and h10) (22,24). The heme is buried in a hydrophobic cleft or pocket formed by the subdomain helices and its position within IB forms a striking superposition on the plane represented by the curved structure assumed by long chain fatty acid when occupying this site (FIG. 2). One half of the pocket is enclosed by h9 and h10, the other half by the loop h8, the top by h7 and the bottom by the loop between h8 and h9. The plane of the inserted heme lies approximately 30 degrees to the helical axes of h9 and h10.

In accordance with the invention, the high resolution crystal structure allowed for the elucidation of the heme binding region in albumin and revealed the key binding regions in this area. In particular, there are five residues that show close interaction with the heme and appear to be key contributors to the high binding affinity, Tyr-161, Ile-142, Tyr-138, His-145, and Lys-190. The tyrosine side chains form close parallel stacking interactions with the heme (FIG. 3). One of the key heme interactions involves Tyr-161, which shows coordination of the phenolic oxygen with the heme iron resulting in an oxygen to heme plane distance of 2.73 Å and a pentacoordinate iron. This phenolic oxygen replaces the chloride ion of the hemin complex in solution ($Fe^{III}$-Protoporphyrin-IX (Cl)). The details of the methemalbumin heme are similar to the original hemin small molecule structure determined in 1965 (25) where: 1) the iron is located off the heme surface (0.475 Å) (the Fe electron bulge in the methemalbumin indicates a similar movement, see FIG. 1); 2) the Chloride to heme plane distance is 2.693 Å (methemalbumin Tyr-161 O to heme plane distance 2.73 Å); and 3) heme potentially disordered (averaged) by the two hemes rotated 180° about a line between the CHA and CHC atoms in both structures. In the methemalbumin structure the Fe atom was restricted to co-planarity with the heme during refinement, however, the difference maps as in FIG. 1, show a significant deviation from planarity, suggesting an iron position similar to the original hemin small molecule structure. If one assumes the iron atom also lies 0.475 Å off the heme surface in methemalbumin, then the Tyr-161 phenyl oxygen to iron distance can be estimated at 2.27 Å, a value in good agreement with the Cl to Fe distance of 2.22 Å in hemin (25). In the more recent malarial pigment β-hematin structure where the carboxylate oxygen of a symmetrically related heme becomes the fifth coordinate to the Fe atom, the O to Fe distance was determined at 1.89 Å (26).

Figure 3A:
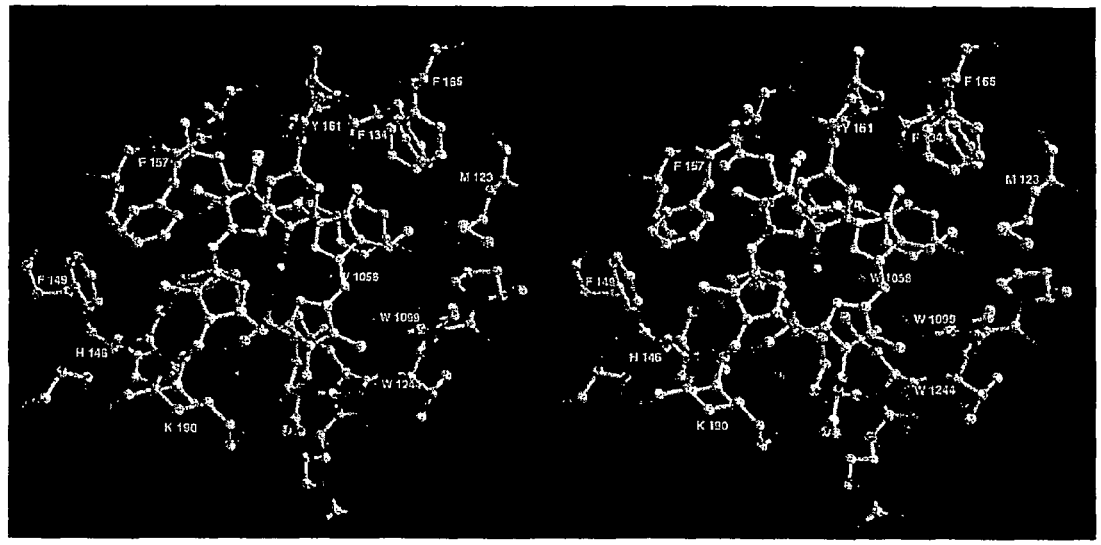
FIG. 3A is a stereo view from the 'proximal' side of the heme showing another perspective of the coordination of the Tyr-161 hydroxyl with the Fe atom and the salt bridge and hydrogen bonding interactions of Lys-190, His-146, and Arg-114. The water molecules located in the binding pocket and associated with Tyr-161 which have been discussed in the text are illustrated.
Figure 3B:
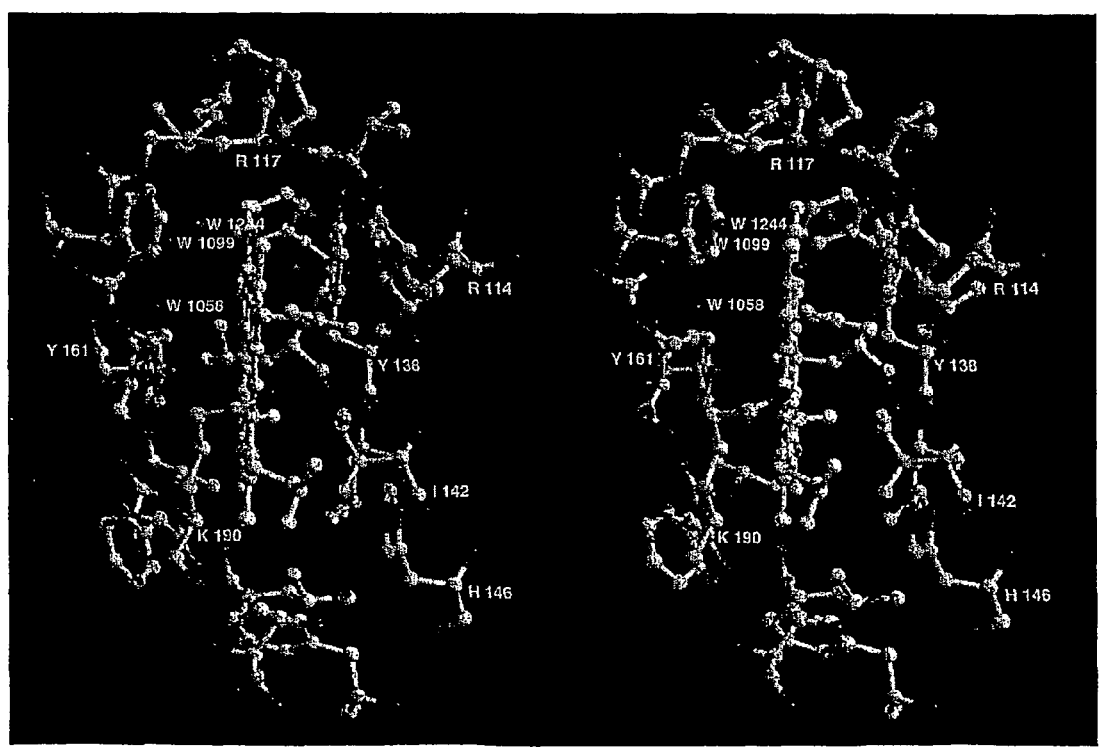
FIG. 3B is a stereo view of the heme pocket as viewed from the surface opening. Close interactions are seen with Ile 142 (right or 'distal' side), Tyr-161 (left or 'proximal' side) and Tyr 138 (top right) within the pocket and the salt bridges with Lys-190, the 'gate' residue and His-146. Note the water coordination and close proximity of Arg-114 to the heme carboxylate (top right).

In addition to the coordination with the heme iron, the phenolic oxygen of Tyr-161 forms hydrogen bonds with a series of water molecules (W1058, W1099, and W1244) within the hydrophobic cavity and extending into a well defined surface water structure (FIG. 3B). In accordance with the invention, this side of the heme is referred to as the "proximal" side. No water molecules were observed on the opposite or 'distal' side of the heme pocket. The propionic residues of the heme protrude from the pocket and form two important salt bridges, one with His-145 which forms a strong bridge with the 'A' ring carboxylate and the other with Lys-190, which forms a salt bridge mid way between both the 'A' and 'D' ring heme carboxyls (FIG. 3). Ile-142, near the iron on the distal side of the heme, contributes one of the closest hydrophobic interactions.

The residues having close interaction or contributing to the hydrophobic surface of the binding pocket include: Tyr-161, Phe-157, Arg-186, Leu-182, Arg-117, Phe-134, Leu-135, Leu-154, Phe-149, Ile-142, His-146, Arg-114, Lys-190, Ser-193, Ala-158, Tyr-138, Leu-115, Met-123, Phe-165, and Pro-118. Details of many of the heme binding interactions of these residues are illustrated in FIG. 3A. In accordance with the invention, a recombinant serum albumin with improved properties can be prepared wherein certain residues contributing to the hydrophobic surface of the binding pocket are replaced with residues having a greater affinity to heme. For example, improved binding properties may be obtained wherein at least one of the these key hydrophobic binding residues in the heme binding region replaced with a hydrophilic binding residue, such as histidine. In addition, the creation of optimal performance may also require the simultaneous replacement of two or more of the defined residues with residues of different charge or hydrophobicity, thereby improving the gas affinity and oxidation rates. These recombinant albumins can be prepared in accordance with the invention in any suitable manner well known in the art including those techniques as set forth in the prior patents and applications set forth above, e.g., wherein nucleic acid coding for the desired mutation is expressed using an appropriate expression vector.

Comparisons of the hemalbumin structure with the native albumin/myristate structure reveal four residues that show pronounced movements upon heme complexation. The first of these is Ile-142 where the CD1 atom has swung about 135° away from the heme plane to avoid steric clash, resulting in a CD1 atom within 3.38 Å from the NA nitrogen. His-146 displays perhaps the largest movement upon complexation, making a key salt bridge with the 'A' ring carboxylate of heme, resulting in an equidistant His NE atom to O1A/O2A distance of 3.30 Å. The third residue demonstrating significant side chain movement is Lys-190. In the HSA-myristate structure, the NZ nitrogen at the end of the side chain of Lys-190 makes a 2.99 Å salt bridge with the OD1 oxygen of Asp-187. In the methemalbumin structure, this salt bridge is broken resulting in the 180° rotation of the Lys-190 side chain about its CD atom across the pocket opening to form a key salt bridge interaction with both the heme carboxyls. This new position was supported by clear difference electron density. In this position, the NZ nitrogen atom of Lys-190 is almost midway between the two heme carboxylate groups and makes a salt bridge with each of them. The shortest (2.99 Å) of these is made with the O2D oxygen of the heme 'D' ring carboxylate, while a slightly longer salt bridge (3.32 Å) is formed between the NZ atom of Lys-190 and the O1A oxygen of the heme 'A' ring carboxylate. The swinging motion by the side chain of Lys-190 can be likened to a gate shutting after the hemin/heme is bound with the salt bridges serving as a latch to keep the gate shut. Arg-114, the fourth residue, has its side chain rotating downward towards the heme, further closing off the entrance to the pocket at the top distal side of the subdomain (FIG. 3B). In this position it appears that the NE atom of Arg-114 makes a long-range hydrogen bond (3.94 Å) with the O1D oxygen atom of the 'D' ring carboxylate.

The basis of interspecies variations in albumin heme binding is further indicated by the high resolution structure of the present invention. As discussed above, there appear to be five residues which show strong or 'key' interactions with the heme: Tyr 161, Ile-142, Tyr-138, His 146, and Lys-190. In mammals all of these residues are either conserved (Tyr-161, Tyr-138, His-146) or substituted with closely homologous residues, i.e., Ile-142 to Val. with the important exception of Lys-190. Lys-190, the 'gate' residue, while present in primate albumins, is replaced with Leu in all of the currently sequenced mammalian albumins. This strongly suggests that the salt bridging interaction of Lys-190 is key to stabilizing and securing the heme within the binding pocket. The importance of this residue is further corroborated by the sequence of bull frog albumin (27), which has retained Lys at 190, and despite its overall low sequence identity with mammalian albumins (21.7%), still retains its heme binding capabilities. The occurrence of Lys, His or Arg at 190 (normalized to the amino acid sequence of human serum albumin), allows the prediction that several other albumins such as hen (28) and the other members of the albumin gene family e.g., alpha-fetoprotein (29) will also be found to harbor an active high affinity heme binding site. Lys-190 may also play an important role the initial 'fast' binding interaction proposed by Adams and Berman (9) followed by the slower internalization of the heme into the hydrophobic pocket. Finally, it should also be considered that the presence of Leu at the pocket opening, may, in addition to eliminating an important charge stabilization, sterically hinder heme access to the pocket.

It is therefore another aspect of the present invention that imparting heme-binding properties into albumins of non-human origin may be achieved by replacing the inactivating equivalent residue (equivalent to residue 190 in human serum albumin) with Lys or His. In many non-human albumins, particularly mammalian albumins, the amino acid residue at the equivalent position of the human aa 190 (as determined by sequence alignment of albumins well known to those skilled in the art and shown, e.g., in Carter et al., (1994), The Structure of Serum Albumin. *Adv. Prot. Chem.*, 45, 153–203, incorporated herein by reference) has a Leu residue instead of Lys. As a result, these albumins do not normally bind to heme, and thus the substitution of Lys for Leu in these non-human albumins at the equivalent position of HSA Lys-190 would result in the imparting of heme-binding properties to non-human albumins, particularly non-human mammalian albumins.

In accordance with the present invention, a method is provided for developing molecules of albumin with improved gas binding properties using the crystal high resolution structure described above. It has long been established that the native hemalbumin complex is inactive as an oxygen binding protein, a property that is now readily understood by the chemistry of the observed structure. Since albumin is the major protein of the circulatory system contributing 80% to osmotic blood pressure and maintenance of blood pH (4) and considered to be the volume expander of choice; it is believed that the development of an oxygen transporting albumin could be of tremendous medical importance. For example, others, in a different approach from the present invention, have produced a modified heme with an axial imidazole base covalently linked to the porphyrin ring (30) which has been shown to reversibly bind oxygen in vitro and in vivo (16, 31–35), although the physical size of FeP probably precludes it from binding to the same high affinity site as hemin.

The atomic structure of methemalbumin as described above provides an essential framework for the development of albumin-based 'blood substitutes' or improved volume expanders with oxygen transport capabilities. The high resolution hemalbumin structures of the invention have allowed for the determination of the key regions which will allow for the creation of genetically engineered albumins with novel gas binding properties. For example, substitution of the selected residues in closest proximity to the heme with histidine, activates the heme to limited reversible oxygen binding in the FeII state (19). As set forth above, these key residues include amino acids Tyr-161, Phe-157, Arg-186, Leu-182, Arg-117, Phe-134, Leu-135, Leu-154, Phe-149, Ile-142, His-146, Arg-114, Lys-190, Ser-193, Ala-158, Tyr-138, Leu-115, Met-123, Phe-165, and Pro-118 of serum albumin.

In accordance with the invention, the provision of the high resolution atomic coordinates of the hemalbumin complex will also allow for the identification of key binding sites such as to permit the development of genetically modified albumin and heme molecules which have maximized gas binding properties. This can be done by examining the high resolution structure with regard to the interface with gases such as oxygen and other potentially toxic gases such as carbon monoxide, nitric acid and cyanide, and by maximizing the ability of the complex to bind with such gases by replacement of residues as necessary to maximize the binding to specific gases. Accordingly, another aspect of the invention will be the improvement of binding, transport, and delivery of therapeutic gases such as oxygen, as well as the scavenging and removal of potentially toxic gases such as cyanide, nitric acid, carbon monoxide, etc.

It is thus submitted that the foregoing embodiments are only illustrative of the claimed invention, and alternative embodiments well known or obvious to one skilled in the art not specifically set forth above also fall within the scope of the claims.

In addition, the following examples are presented as illustrative of the claimed invention, or aspects associated with the present invention, and are not deemed to be limiting of the scope of the invention in any manner.

EXAMPLES

Example 1

Obtaining the High Resolution Structure of the Hemalbumin Complex

Overview:

The high resolution structure of hemalbumin was determined by single crystal X-ray diffraction to a resolution of 1.9 Å. The structure revealed the protoporphyrin IX bound to a single site within a hydrophobic cavity in subdomain IB, one of the principal binding sites for long chain fatty acid. The iron is penta coordinated with the fifth ligand comprised of the hydroxyloxygen of Tyr-161 (phenolic oxygen to heme plane distance: 2.73 Å) in an otherwise completely hydrophobic pocket. The heme propionic acid residues form salt bridges with His-142 and Lys-190, which together with a series of hydrophobic interactions, enclose and secure the heme within the IB helical motif. A detailed discussion of the structure together with its implications for the development of potential blood substitutes is presented.

Materials and Methods

The hemalbumin crystals were prepared in a manner previously described (19,20), with the following exception, the human albumin, defatted after Chen (21) was coupled with 1:1 molar ratio of albumin:hemin ($Fe^{III}$-Protoporphyrin-IX (Cl)) prior to coupling with myristate. The crystals are of the same C2 form as the form-III of our previous report (19). Diffraction data were collected at the Beamline 5.0.3 of the Advanced Light Source (ALS), Lawrence Berkeley Laboratory (LBL). A 2×2 array (ADSC) of CCD detectors was used with a detector-to-crystal distance of 180 mm. A total of 180 (1°) oscillation images were collected from one crystal at 100 K using photon wavelength of 1.0 Å and exposure of 60 second per frame. At the cryogenic temperature, the unit cell dimensions were a=183.11 Å, b=37.91 Å, c=94.83 Å, β=105.04°. These images yielded a data set of 44,335 independent reflections with positive intensities to a resolution of 1.9 Å ($R_{merge}$: 3.7%; average multiplicity: 2.03; average I/σ(I): 14.7, and completeness: 88.1%).

The program package of CNX X-ray from Accelrys, Inc. was used for structure refinement, with the protein starting model taken from a structure of human albumin complexed with myristate (without hemin) determined in our earlier studies (19,22) and re-refined more recently at 100 K (unpublished). The hemin and five myristate molecules were clearly resolved in the difference density maps after initial refinement. When hemin, myristates, and solvent water molecules were incorporated in the model, the refinement quickly converged to an R-factor of 22.8% for all 42,107 reflections in the working set with no sigma cut-off (R-free 28.2%), yielding a structure of good geometry giving rms deviations from ideality of 0.005 Å for bond-distance and 1.190 for valence-angle (Table I). The final model includes 583 protein residues, 1 hemin molecule, 5 myristic acid molecules and 581 solvent water molecules with an average B-factor of 27.8 Å² for the protein atoms. One residue each at both N- and C-termini were not visible on the electron density maps, presumably disordered, and were not included in the model. Atomic coordinates of the methemalbumin structure are provided herein in Appendix A.

TABLE I

Data collection and model refinement statistics

| Data collection | |
|---|---|
| Space group | C2 |
| a (Å) | 183.116 |
| b (Å) | 37.909 |
| c (Å) | 94.832 |
| β (°) | 105.036 |
| Resolution range (Å) | 50–1.9 (1.97–1.9)[a] |
| Independent reflections | 45,420 |
| Multiplicity | 2.6 |
| Completeness (%) | 83.5 (56.3)[a] |
| I/σ$_I$[b] | 14.7 |
| $R_{sym}$ (%)[c] | 3.7 (26.6)[a] |
| Number of crystals used | 1 |
| Temperature of data collection (K) | 100 |
| X-ray wavelength (Å) | 1.0 |
| Model refinement | |
| Number of non-hydrogen atoms | 4,759 |
| Number of water molecules | 581 |
| $R_{work}$ (%)[d] | 22.8 |
| $R_{free}$ (%)[e] | 28.2 |
| rms[f] deviation from ideal bond lengths (Å) | 0.005 |
| rms deviation from ideal bond angles (°) | 1.19 |
| rms deviation in B-factors main/side chain (Å) | 1.382/2.327 |
| Average B-factor (Å²) | 27.8 |

[a]Values in parentheses indicate the highest resolution shell.
[b]No I/σ$_I$ cutoff was used in the refinement.
[c]$R_{sym} = \Sigma|(I_{hkl}) - <I>|/\Sigma(I_{hkl})$, where $I_{hkl}$ is the integrated intensity of a given reflection.
[d]$R_{work} = \Sigma_{hkl}|F_{obs} - F_{calc}|/\Sigma_{hkl}F_{obs}$ where $F_{obs}$ and $F_{calc}$ are the observed and calculated structure factors, respectively (identical to $R_{cryst}$).
[e]$R_{free}$ is the $R_{work}$ calculated using a randomly selected 5% sample of reflection data omitted from the refinement.
[f]rms means root mean square.

Results and Discussion

The current hemalbumin structure is well determined and represents the highest resolution albumin structure reported to date. Details of the refinement statistics have been given in Table I. The quality of the resulting electron density is high providing detailed information of the heme binding interaction as well as other important structural information such as positions of key water molecules. The orientation of the heme ($Fe^{III}$-Protoporphyrin-IX) provides a good fit to the electron density as shown in FIG. 1. There is the possibility that a mixture of the two orientations actually exists in the complex (180 degree rotational isomers along the CHA to CHC line). However, the orientation chosen provides the best fit, and neither orientation affects the resulting interpretation of the binding chemistry. The overall structure of methemalbumin is very similar to the HSA-myristate structure we have previously determined and used in this work to derive the phases for the methemalbumin structure (discussed above); and the structure using the same crystal forms and reported by others (23). The structures are essentially identical, having a rms deviation between Cα atom of positions of 0.396 Å. When Cα for residues 109–195 that constitute the IB subdomain are superimposed, the rms was 0.32 Å.

A single site for hemin revealed by earlier lower resolution studies (19) was verified by this high resolution study. The hemin is located within the IB subdomain which is constituted by a loop and four contiguous helices (h7, h8, h9 and h10) (22,24). The heme is buried in a hydrophobic cleft or pocket formed by the subdomain helices and its position within IB forms a striking superposition on the plane represented by the curved structure assumed by long chain fatty acid when occupying this site (FIG. 2). One half of the pocket is enclosed by h9 and h10, the other half by the loop h8, the top by h7 and the bottom by the loop between h8 and h9. The plane of the inserted heme lies approximately 30 degrees to the helical axes of h9 and h10.

There are five residues that show close interaction with the heme and appear to be key contributors to the high binding affinity, Tyr-161, Ile-142, Tyr-138, His-145, and Lys-190. The tyrosine side chains form close parallel stacking interactions with the heme (FIG. 3). The most interesting heme interaction involves Tyr-161, which shows coordination of the phenolic oxygen with the heme iron resulting in an oxygen to heme plane distance of 2.73 Å and a penta-coordinate iron. This phenolic oxygen replaces the chloride ion of the hemin complex in solution ($Fe^{III}$-Protoporphyrin-IX (Cl)). The details of the methemalbumin heme are similar to the original hemin small molecule structure determined in 1965 (25) where: 1) the iron is located off the heme surface (0.475 Å) (the Fe electron bulge in the methemalbumin indicates a similar movement, see FIG. 1); 2) the Chloride to heme plane distance is 2.693 Å (methemalbumin Tyr-161 O to heme plane distance 2.73 Å); and 3) heme potentially disordered (averaged) by the two hemes rotated 180° about a line between the CHA and CHC atoms in both structures. In the methemalbumin structure the Fe atom was restricted to co-planarity with the heme during refinement, however, the difference maps as in FIG. 1, show a significant deviation from planarity, suggesting an iron position similar to the original hemin small molecule structure. If one assumes the iron atom also lies 0.475 Å off the heme surface in methemalbumin, then the Tyr-161 phenyl oxygen to iron distance can be estimated at 2.27 Å, a value in good agreement with the Cl to Fe distance of 2.22 Å in hemin (25). In the more recent malarial pigment β-hematin structure where the carboxylate oxygen of a symmetrically related heme becomes the fifth coordinate to the Fe atom, the O to Fe distance was determined at 1.89 Å (26).

In addition to the coordination with the heme iron, the phenolic oxygen of Tyr-161 forms hydrogen bonds with a series of water molecules (W1058, W1099, and W1244) within the hydrophobic cavity and extending into a well defined surface water structure (FIG. 3B). We shall, for the sake of this example, refer to this side of the heme as the "proximal" side. No water molecules were observed on the opposite or 'distal' side of the heme pocket. The propionic residues of the heme protrude from the pocket and form two important salt bridges, one with His-145 which forms a strong bridge with the 'A' ring carboxylate and the other with Lys-190, which forms a salt bridge mid way between both the 'A' and 'D' ring heme carboxyls (FIG. 3). Ile-142, near the iron on the distal side of the heme, contributes one of the closest hydrophobic interactions.

A list of the residues having close interaction or contributing to the hydrophobic surface of the binding pocket are: Tyr-161, Phe-157, Arg-186, Leu-182, Arg-117, Phe-134, Leu-135, Leu-154, Phe-149, Ile-142, His-146, Arg-114, Lys-190, Ser-193, Ala-158, Tyr-138, Leu-115, Met-123, Phe-165, and Pro-118. Details of many of the heme binding interactions of these residues are illustrated in FIG. 3.

Comparisons of the hemalbumin structure with the native albumin/myristate structure reveal four residues that show pronounced movements upon heme complexation. The first of these is Ile-142 where the CD1 atom has swung about 135° away from the heme plane to avoid steric clash, resulting in a CD1 atom within 3.38 Å from the NA nitrogen. His-146 displays perhaps the largest movement upon complexation, making a key salt bridge with the 'A' ring carboxylate of heme, resulting in an equidistant His NE atom to O1A/O2A distance of 3.30 Å. The third residue demonstrating significant side chain movement is Lys-190. In the HSA-myristate structure, the NZ nitrogen at the end of the side chain of Lys-190 makes a 2.99 Å salt bridge with the OD1 oxygen of Asp-187. In the methemalbumin structure, this salt bridge is broken resulting in the 180° rotation of the Lys-190 side chain about its CD atom across the pocket opening to form a key salt bridge interaction with both the heme carboxyls. This new position was supported by clear difference electron density. In this position, the NZ nitrogen atom of Lys-190 is almost midway between the two heme carboxylate groups and makes a salt bridge with each of them. The shortest (2.99 Å) of these is made with the O2D oxygen of the heme 'D' ring carboxylate, while a slightly longer salt bridge (3.32 Å) is formed between the NZ atom of Lys-190 and the O1A oxygen of the heme 'A' ring carboxylate. The swinging motion by the side chain of Lys-190 can be likened to a gate shutting after the hemin/heme is bound with the salt bridges serving as a latch to keep the gate shut. Arg-114, the fourth residue, has its side chain rotating downward towards the heme, further closing off the entrance to the pocket at the top distal side of the subdomain (FIG. 3B). In this position it appears that the NE atom of Arg-114 makes a long-range hydrogen bond (3.94 Å) with the O1D oxygen atom of the 'D' ring carboxylate.

Structural Basis of Interspecies Differences in Hemin Binding

The basis of interspecies variations in albumin heme binding is clearly indicated by this structure. As discussed in the previous section, there are essentially five residues, which show strong or 'key' interactions with the heme: Tyr 161, Ile-142, Tyr-138, His 146, and Lys-190. In mammals all of these residues are either conserved (Tyr-161, Tyr-138, His-146) or substituted with closely homologous residues, i.e., Ile-142 to Val. with the important exception of Lys-190.

Lys-190, the 'gate' residue, while present in primate albumins, is replaced with Leu in all of the currently sequenced mammalian albumins. This strongly suggests that the salt bridging interaction of Lys-190 is key to stabilizing and securing the heme within the binding pocket. The importance of this residue is further corroborated by the sequence of bull frog albumin (27), which has retained Lys at 190, and despite its overall low sequence identity with mammalian albumins (21.7%), still retains its heme binding capabilities. The occurrence of Lys, His or Arg at 190 (normalized to the amino acid sequence of human serum albumin), allows the prediction that several other albumins such as hen (28) and the other members of the albumin gene family e.g., alpha-fetoprotein (29) will also be found to harbor an active high affinity heme binding site. It may be further the case that Lys-190 plays an important role the initial 'fast' binding interaction proposed by Adams and Berman (9) followed by the slower internalization of the heme into the hydrophobic pocket. Finally, it should also be considered that the presence of Leu at the pocket opening, may, in addition to eliminating an important charge stabilization, sterically hinder heme access to the pocket.

Implications For the Creation of Albumins with Novel Gas Binding Properties

It has long been established that the native hemalbumin complex is inactive as an oxygen binding protein, a property that is now readily understood by the chemistry of the observed structure. Since albumin is the major protein of the circulatory system contributing 80% to osmotic blood pressure and maintenance of blood pH (4) and considered to be the volume expander of choice; it is believed that the further development and refinement of an oxygen transporting albumin (such as disclosed in U.S. Pat. No. 5,948,609) could be of tremendous medical importance.

For example, others, in a different approach from the present invention, have produced a modified heme with an axial imidazole base covalently linked to the porphyrin ring (30) which has been shown to reversibly bind oxygen in vitro and in vivo (16, 31–35), although the physical size of FeP probably precludes it from binding to the same high affinity site as hemin. The atomic structure of methemalbumin in accordance with the invention thus provides an essential framework for the development of albumin-based 'blood substitutes' or improved volume expanders with oxygen transport capabilities. The hemalbumin complexes have successfully guided the creation of genetically engineered albumins with novel gas binding properties. For example, simple substitution of the selected residues in closest proximity to the heme with histidine, activates the heme to limited reversible oxygen binding in the FeII state (19) and/or imparts high affinity to CN in the oxidized $Fe^{III}$ form.

In general, the high resolution structure revealed numerous previously unappreciated components of the interaction of albumin with protoporphyrins. For example we now understand the species variation in heme binding or lack thereof.

We also understand which side of the pocket provides the distal and proximal interactions to the heme, the role and accessible surface to water molecules, the residues important in creating the high affinity to the heme and many many other exacting points relevant to therapeutic development.

Accordingly, It should be understood by one skilled in the art that this information may now make possible various ab initio calculations to design and improve heme or oxygen binding or any other methods of therapeutic development (since these are now the highest resolution human albumin coordinates). The present invention can thus be used to guide rational drug design of therapeutic compounds associated with the hemalbumin complex, in terms of drugs that can inhibit or enhance certain functions, or in terms of products such as recombinant forms of hemalbumin which can be constructed to reversibly bind oxygen.

REFERENCES

The following citations are incorporated by reference as if set forth in full herein:
1. Hrkal, Z., Vodrazka, Z., and Kalousek, I. (1974). Transfer of heme from ferrihemoglobin and ferrihemoglobin isolated chains to hemopexin. *Eur. J. Biochem.* 43, 73–78.
2. Muller-Eberhard, U., Bosman, C., and Liem, H. H. (1970). Tissue localization of the heme-hemopexin complex in the rabbit and the rat as studied by light microscopy with the use of radioisotopes. *J. Lab Clin. Med.* 76,426–431.
3. Naitoh, Y., Taketani, S., Tokunaga, R., and Sameshima, Y. (1988). Mechanisms involved in the cellular uptake of hematoporphyrin by rat hepatoma cells. *J. Biochem.* (Tokyo) 103, 973–978.
4. Peters, T., Jr. (1996) All about albumin. Biochemistry, genetics, and medical applications, Academic Press.
5. Seery, V. L. and Muller-Eberhard, U. (1973). Binding of porphyrins to rabbit hemopexin and albumin. *J. Biol. Chem.* 248, 3796–3800.
6. Hrkal, Z., Kodicek, M., Vodrazka, Z., Meloun, B., and Moravek, L. (1978). Haeme binding to human serum albumin and to the three large cyanogen bromide albumin fragments. *Int. J. Biochem.* 9, 349–355.
7. Hrkal, Z., Kalousek, I., and Vodrazka, Z. (1980). Haeme binding to albumin and equilibria in the albumin-ferrihaemoglobin and albumin-haemopexin systems. *Int. J. Biochem.* 12, 619–624.
8. Adams, P. A., Goold, R. D., and Thumser, A. A. (1989). Heme-peptide/protein interactions: the binding of heme octa and undecapeptides, and microperoxidase-8 and -11, to human serum albumin. *J. Inorg. Biochem.* 37, 91–103.
9. Adams, P. A. and Berman; M. C. (1980). Kinetics and mechanism of the interaction between human serum albumin and monomeric haemin. *Biochem. J.* 191, 95–102.
10. Parr, G. R. and Pasternack, R. F. (1977). The interaction of some water-soluble porphyrins and metalloporphyrins with human serum albumin. *Bioinorg. Chem.* 7, 277–282.
11. Baroni, S., Mattu, M., Vannini, A., Cipollone, R., Aime, S., Ascenzi, P., and Fasano, M. (2001). Effect of ibuprofen and warfarin on the allosteric properties of haem-human serum albumin. A spectroscopic study. *Eur. J. Biochem.* 268, 6214–6220.
12. Bearden, A. J., Morgan, W. T., and Muller-Eberhard, U. (1974). Heme complexes of rabbit hemopexin, human hemopexin and human serum albumin: electron spin resonance and Mossbauer spectroscopic studies. *Biochem. Biophys. Res. Commun.* 61, 265–272.
13. Beaven, G. H., Chen, S. H., d' Albis, A., and Gratzer, W. B. (1974). A spectroscopic study of the haemin—human-serum-albumin system. *Eur. J. Biochem.* 41, 539–546.
14. Casella, L., Gullotti, M., Poli, S., and DeGioia, L. (1993). Haem-Protein Interactions. The Binding of Haem Complexes to Serum Albumin. *Gazzetta Chimica Italiana* 123, 149–154.
15. Fasano, M., Baroni, S., Vannini, A., Ascenzi, P., and Aime, S. (2001). Relaxometric characterization of human hemalbumin. *J. Biol. Inorg. Chem.* 6, 650–658.

16. Komatsu, T., Matsukawa, Y., and Tsuchida, E. (2000). Kinetics of CO and O(2) binding to human serum albumin-heme hybrid. *Bioconjug. Chem.* 11, 772–776.
17. Mattu, M., Vannin, A., Coletta, M., Fasano, M., and Ascenzi, P. (2001). Effect of bezafibrate and clofibrate on the heme-iron geometry of ferrous nitrosylated heme-human serum albumin: an EPR study. *J. Inorg. Biochem.* 84, 293–296.
18. Dockal, M., Carter, D. C., and Ruker, F. (1999) The three recombinant domains of human serum albumin. Structural characterization and ligand binding properties. *J. Biol. Chem.* 274(41), 29303–29310.
19. Carter, D. C., Ho, J. X., and Ruker, F. (1999) Oxygen-transporting albumin-based blood replacement composition and blood volume expander. U.S. Pat. No. 5,948,609.
20. Carter, D. C., Chang, B., Ho, J. X., Keeling, K., and Krishnasami, Z. (1994). Preliminary crystallographic studies of four crystal forms of serum albumin. *Eur. J. Biochem.* 226, 1049–1052.
21. Chen, R. F. (1967). Removal of fatty acids from serum albumin by charcoal treatment. *J. Biol. Chem.* 242, 173–181.
22. Carter, D. C. and Ho. J. X. (1994) The Structure of Serum Albumin. *Adv. Prot. Chem.,* 45, 153–203, V. Schumaker, ed. Academic Press.
23. Curry, S., Mandelkow, H., Brick, P., and Franks, N. (1998). Crystal structure of human serum albumin complexed with fatty acid reveals an asymmetric distribution of binding sites. *Nat Struct. Biol.* 5, 827–835.
24. He, X. M. and Carter, D. C. (1992). Atomic structure and chemistry of human serum albumin. *Nature* 358, 209–215.
25. Keonig, D. F. (1965) The structure of α-chlorohemin. *Acta Cryst* 18, 663–673.
26. Pagola, S., Stephens, P. W., Bohle, D. S., Kosar, A. D., and Madsen, S. K. (2001) The structure of malaria pigment β-haematin. *Nature* 404, 307–310.
27. Averyhart-Fullard, V. and Jaffe, R. C. (1990). Cloning and thyroid hormone regulation of albumin mRNA in Rana catesbeiana tadpole liver. *Mol. Endocrinol.* 4, 1556–1563.
28. Cassady, A. I. (1991) GeneBank Database Accession #63748.
29. Morinaga, T., Sakai, M., Wegmann, T. G., and Tamaoki, T. (1983) Primary structure of human alpha-fetoprotein and its mRNA, *Proc. Natl. Acad. Sci. U.S.A.* 80, 4604–4608.
30. Tsuchida, E., Ando, K., Maejima, H., Kawai, N., Komatsu, T., Takeoka, S., and Nishide, H. (1997). Properties of and oxygen binding by albumin-tetraphenylporphyrinatoiron(II) derivative complexes. *Bioconjug. Chem.* 8, 534–538.
31. Nakagawa, A., Komatsu, T., and Tsuchida, E. (2001). Photoreduction of autooxidized albumin-heme hybrid in saline solution: revival of its O(2)-binding ability. *Bioconjug. Chem.* 12, 648–652.
32. Tsuchida, E., Komatsu, T., Matsukawa, Y., Hamamatsu, K., and Wu, J. (1999). Human serum albumin incorporating Tetrakis(o-pivalamido) phenylporphinatoiron(II) derivative as a totally synthetic O2-carrying hemoprotein. *Bioconjug. Chem.* 10, 797–802.
33. Tsuchida, E., Komatsu, T., Hamamatsu, K., Matsukawa, Y., Tajima, A., Yoshizu, A., Izumi, Y., and Kobayashi, K. (2000). Exchange transfusion with albumin-heme as an artificial O2-infusion into anesthetized rats: physiological responses, O2-delivery, and reduction of the oxidized hemin sites by red blood cells. *Bioconjug. Chem.* 11, 46–50.
34. Komatsu, T., Hamamatsu, K., Takeoka, S., Nishide, H., and Tsuchida, E. (1 98). Human serum albumin-bound synthetic hemes as an oxygen carrier: determination of equilibrium constants for heme binding to host albumin. *Artif Cells Blood Substit. Immobil. Biotechnol.* 26, 519–527.
35. Komatsu, T., Hamamatsu, K., Wu, J., and Tsuchida, E. (1999). Physicochemical properties and O2-coordination structure of human serum albumin incorporating tetrakis (o-pivalamido)phenylporphyrinatoiron(II) derivatives. *Bioconjug. Chem.* 10, 82–86.

Appendix A

List of atomic coordinates of subdomain IB of human albumin and heme.

Note:

(1) Atomic coordinates list is part of the ternary complex crystal structure of human albumin, heme and myristate;
(2) Crystal form is of space group of C2 (with b as unique axis) with cell dimensions of a=183.1 A, b=37.9 A, c=94.8 A, (=105.0 (;
(3) The orthogonal coordinates span in the Cartesian coordinate system which conforms to the same convention as that of the Protein Data Bank;
(4) List also includes selected solvent water molecules Involved in interactions with heme.

| ATOM | 852 | N | ASN | 109 | 34.561 | −7.463 | 27.701 | 1.00 | 37.28 | N |
|---|---|---|---|---|---|---|---|---|---|---|
| ATOM | 853 | CA | ASN | 109 | 33.707 | −7.643 | 28.877 | 1.00 | 38.81 | C |
| ATOM | 854 | CB | ASN | 109 | 32.588 | −8.649 | 28.585 | 1.00 | 41.49 | C |
| ATOM | 855 | CG | ASN | 109 | 31.563 | −8.724 | 29.708 | 1.00 | 44.62 | C |
| ATOM | 856 | OD1 | ASN | 109 | 31.914 | −8.880 | 30.877 | 1.00 | 47.83 | O |
| ATOM | 857 | ND2 | ASN | 109 | 30.288 | −8.621 | 29.354 | 1.00 | 46.00 | N |
| ATOM | 858 | C | ASN | 109 | 34.612 | −8.186 | 29.979 | 1.00 | 37.18 | C |
| ATOM | 859 | O | ASN | 109 | 34.498 | −9.345 | 30.362 | 1.00 | 38.56 | O |
| ATOM | 860 | N | PRO | 110 | 35.529 | −7.346 | 30.491 | 1.00 | 35.52 | N |
| ATOM | 861 | CD | PRO | 110 | 35.650 | −5.926 | 30.108 | 1.00 | 34.37 | C |
| ATOM | 862 | CA | PRO | 110 | 36.495 | −7.677 | 31.546 | 1.00 | 35.82 | C |
| ATOM | 863 | CB | PRO | 110 | 37.407 | −6.452 | 31.564 | 1.00 | 34.23 | C |
| ATOM | 864 | CG | PRO | 110 | 36.464 | −5.347 | 31.256 | 1.00 | 35.17 | C |
| ATOM | 865 | C | PRO | 110 | 35.915 | −7.988 | 32.927 | 1.00 | 36.43 | C |
| ATOM | 866 | O | PRO | 110 | 36.652 | −8.235 | 33.877 | 1.00 | 38.59 | O |
| ATOM | 867 | N | ASN | 111 | 34.591 | −7.979 | 33.020 | 1.00 | 36.82 | N |
| ATOM | 868 | CA | ASN | 111 | 33.897 | −8.257 | 34.273 | 1.00 | 37.30 | C |

-continued

| | | | | | | | | | |
|---|---|---|---|---|---|---|---|---|---|
| ATOM | 869 | CB | ASN | 111 | 33.908 | −9.763 | 34.550 | 1.00 | 39.93 | C |
| ATOM | 870 | CG | ASN | 111 | 33.026 | −10.538 | 33.583 | 1.00 | 42.45 | C |
| ATOM | 871 | OD1 | ASN | 111 | 31.831 | −10.255 | 33.458 | 1.00 | 42.90 | O |
| ATOM | 872 | ND2 | ASN | 111 | 33.611 | −11.507 | 32.890 | 1.00 | 44.99 | N |
| ATOM | 873 | C | ASN | 111 | 34.432 | −7.483 | 35.472 | 1.00 | 36.36 | C |
| ATOM | 874 | O | ASN | 111 | 34.707 | −8.044 | 36.538 | 1.00 | 38.31 | O |
| ATOM | 875 | N | LEU | 112 | 34.580 | −6.179 | 35.291 | 1.00 | 33.54 | N |
| ATOM | 876 | CA | LEU | 112 | 35.027 | −5.300 | 36.351 | 1.00 | 30.14 | C |
| ATOM | 877 | CB | LEU | 112 | 35.866 | −4.147 | 35.774 | 1.00 | 31.52 | C |
| ATOM | 878 | CG | LEU | 112 | 37.256 | −4.418 | 35.198 | 1.00 | 32.24 | C |
| ATOM | 879 | CD1 | LEU | 112 | 37.696 | −3.245 | 34.311 | 1.00 | 32.84 | C |
| ATOM | 880 | CD2 | LEU | 112 | 38.239 | −4.610 | 36.337 | 1.00 | 33.20 | C |
| ATOM | 881 | C | LEU | 112 | 33.761 | −4.719 | 36.988 | 1.00 | 27.71 | C |
| ATOM | 882 | O | LEU | 112 | 32.703 | −4.687 | 36.347 | 1.00 | 25.69 | O |
| ATOM | 883 | N | PRO | 113 | 33.839 | −4.262 | 38.256 | 1.00 | 27.01 | N |
| ATOM | 884 | CD | PRO | 113 | 34.990 | −4.290 | 39.179 | 1.00 | 26.45 | C |
| ATOM | 885 | CA | PRO | 113 | 32.650 | −3.684 | 38.906 | 1.00 | 27.36 | C |
| ATOM | 886 | CB | PRO | 113 | 33.163 | −3.283 | 40.290 | 1.00 | 26.92 | C |
| ATOM | 887 | CG | PRO | 113 | 34.312 | −4.241 | 40.538 | 1.00 | 30.79 | C |
| ATOM | 888 | C | PRO | 113 | 32.207 | −2.469 | 38.100 | 1.00 | 26.20 | C |
| ATOM | 889 | O | PRO | 113 | 33.029 | −1.754 | 37.536 | 1.00 | 27.92 | O |
| ATOM | 890 | N | ARG | 114 | 30.906 | −2.233 | 38.055 | 1.00 | 26.82 | N |
| ATOM | 891 | CA | ARG | 114 | 30.386 | −1.103 | 37.303 | 1.00 | 30.05 | C |
| ATOM | 892 | CB | ARG | 114 | 28.870 | −1.243 | 37.160 | 1.00 | 32.33 | C |
| ATOM | 893 | CG | ARG | 114 | 28.323 | −0.815 | 35.809 | 1.00 | 40.32 | C |
| ATOM | 894 | CD | ARG | 114 | 26.891 | −1.299 | 35.582 | 1.00 | 44.41 | C |
| ATOM | 895 | NE | ARG | 114 | 25.976 | −0.804 | 36.602 | 1.00 | 49.10 | N |
| ATOM | 896 | CZ | ARG | 114 | 24.659 | −0.972 | 36.557 | 1.00 | 51.47 | C |
| ATOM | 897 | NH1 | ARG | 114 | 23.885 | −0.488 | 37.524 | 1.00 | 53.34 | N |
| ATOM | 898 | NH2 | ARG | 114 | 24.114 | −1.632 | 35.545 | 1.00 | 53.41 | N |
| ATOM | 899 | C | ARG | 114 | 30.746 | 0.178 | 38.056 | 1.00 | 29.43 | C |
| ATOM | 900 | O | ARG | 114 | 30.750 | 0.198 | 39.290 | 1.00 | 26.16 | O |
| ATOM | 901 | N | LEU | 115 | 31.071 | 1.239 | 37.322 | 1.00 | 27.53 | N |
| ATOM | 902 | CA | LEU | 115 | 31.415 | 2.508 | 37.942 | 1.00 | 26.31 | C |
| ATOM | 903 | CB | LEU | 115 | 31.997 | 3.484 | 36.921 | 1.00 | 24.86 | C |
| ATOM | 904 | CG | LEU | 115 | 33.355 | 3.144 | 36.308 | 1.00 | 26.44 | C |
| ATOM | 905 | CD1 | LEU | 115 | 33.785 | 4.258 | 35.361 | 1.00 | 25.22 | C |
| ATOM | 906 | CD2 | LEU | 115 | 34.385 | 2.959 | 37.413 | 1.00 | 27.00 | C |
| ATOM | 907 | C | LEU | 115 | 30.164 | 3.118 | 38.542 | 1.00 | 26.77 | C |
| ATOM | 908 | O | LEU | 115 | 29.091 | 3.061 | 37.949 | 1.00 | 27.27 | O |
| ATOM | 909 | N | VAL | 116 | 30.309 | 3.697 | 39.726 | 1.00 | 27.29 | N |
| ATOM | 910 | CA | VAL | 116 | 29.182 | 4.333 | 40.383 | 1.00 | 28.84 | C |
| ATOM | 911 | CB | VAL | 116 | 28.845 | 3.642 | 41.721 | 1.00 | 31.05 | C |
| ATOM | 912 | CG1 | VAL | 116 | 28.583 | 2.150 | 41.488 | 1.00 | 33.07 | C |
| ATOM | 913 | CG2 | VAL | 116 | 29.970 | 3.858 | 42.721 | 1.00 | 31.47 | C |
| ATOM | 914 | C | VAL | 116 | 29.494 | 5.803 | 40.639 | 1.00 | 28.00 | C |
| ATOM | 915 | O | VAL | 116 | 30.611 | 6.171 | 40.996 | 1.00 | 27.97 | O |
| ATOM | 916 | N | ARG | 117 | 28.491 | 6.641 | 40.452 | 1.00 | 28.04 | N |
| ATOM | 917 | CA | ARG | 117 | 28.650 | 8.070 | 40.657 | 1.00 | 27.31 | C |
| ATOM | 918 | CB | ARG | 117 | 27.482 | 8.800 | 40.002 | 1.00 | 27.89 | C |
| ATOM | 919 | CG | ARG | 117 | 27.532 | 10.302 | 40.108 | 1.00 | 26.30 | C |
| ATOM | 920 | CD | ARG | 117 | 26.247 | 10.892 | 39.561 | 1.00 | 27.94 | C |
| ATOM | 921 | NE | ARG | 117 | 26.047 | 10.573 | 38.150 | 1.00 | 29.94 | N |
| ATOM | 922 | CZ | ARG | 117 | 24.988 | 10.950 | 37.439 | 1.00 | 30.00 | C |
| ATOM | 923 | NH1 | ARG | 117 | 24.898 | 10.616 | 36.162 | 1.00 | 28.86 | N |
| ATOM | 924 | NH2 | ARG | 117 | 24.015 | 11.656 | 38.006 | 1.00 | 29.25 | N |
| ATOM | 925 | C | ARG | 117 | 28.724 | 8.412 | 42.144 | 1.00 | 27.03 | C |
| ATOM | 926 | O | ARG | 117 | 27.794 | 8.138 | 42.903 | 1.00 | 25.34 | O |
| ATOM | 927 | N | PRO | 118 | 29.847 | 9.005 | 42.584 | 1.00 | 27.40 | N |
| ATOM | 928 | CD | PRO | 118 | 31.093 | 9.250 | 41.841 | 1.00 | 27.56 | C |
| ATOM | 929 | CA | PRO | 118 | 30.001 | 9.372 | 43.995 | 1.00 | 27.93 | C |
| ATOM | 930 | CB | PRO | 118 | 31.465 | 9.805 | 44.091 | 1.00 | 28.17 | C |
| ATOM | 931 | CG | PRO | 118 | 32.123 | 9.101 | 42.920 | 1.00 | 29.07 | C |
| ATOM | 932 | C | PRO | 118 | 29.071 | 10.527 | 44.310 | 1.00 | 28.14 | C |
| ATOM | 933 | O | PRO | 118 | 28.434 | 11.083 | 43.411 | 1.00 | 27.59 | O |
| ATOM | 934 | N | GLU | 119 | 28.984 | 10.883 | 45.586 | 1.00 | 28.20 | N |
| ATOM | 935 | CA | GLU | 119 | 28.155 | 12.007 | 45.970 | 1.00 | 29.04 | C |
| ATOM | 936 | CB | GLU | 119 | 28.028 | 12.090 | 47.491 | 1.00 | 31.35 | C |
| ATOM | 937 | CG | GLU | 119 | 27.071 | 11.066 | 48.078 | 1.00 | 34.74 | C |
| ATOM | 938 | CD | GLU | 119 | 25.721 | 11.093 | 47.390 | 1.00 | 37.65 | C |
| ATOM | 939 | OE1 | GLU | 119 | 25.511 | 10.298 | 46.446 | 1.00 | 39.19 | O |
| ATOM | 940 | OE2 | GLU | 119 | 24.874 | 11.926 | 47.780 | 1.00 | 38.84 | O |
| ATOM | 941 | C | GLU | 119 | 28.851 | 13.250 | 45.428 | 1.00 | 27.64 | C |
| ATOM | 942 | O | GLU | 119 | 30.077 | 13.288 | 45.326 | 1.00 | 25.66 | O |
| ATOM | 943 | N | VAL | 120 | 28.062 | 14.257 | 45.073 | 1.00 | 27.22 | N |
| ATOM | 944 | CA | VAL | 120 | 28.588 | 15.502 | 44.525 | 1.00 | 26.74 | C |
| ATOM | 945 | CB | VAL | 120 | 27.454 | 16.533 | 44.357 | 1.00 | 26.55 | C |
| ATOM | 946 | CG1 | VAL | 120 | 28.018 | 17.882 | 43.931 | 1.00 | 25.02 | C |
| ATOM | 947 | CG2 | VAL | 120 | 26.455 | 16.021 | 43.339 | 1.00 | 27.22 | C |

-continued

| | | | | | | | | | |
|---|---|---|---|---|---|---|---|---|---|
| ATOM | 948 | C | VAL | 120 | 29.700 | 16.130 | 45.366 | 1.00 | 26.28 C |
| ATOM | 949 | O | VAL | 120 | 30.726 | 16.557 | 44.831 | 1.00 | 24.35 O |
| ATOM | 950 | N | ASP | 121 | 29.491 | 16.202 | 46.679 | 1.00 | 24.10 N |
| ATOM | 951 | CA | ASP | 121 | 30.488 | 16.796 | 47.563 | 1.00 | 26.11 C |
| ATOM | 952 | CB | ASP | 121 | 29.989 | 16.788 | 49.011 | 1.00 | 32.56 C |
| ATOM | 953 | CG | ASP | 121 | 28.756 | 17.648 | 49.209 | 1.00 | 37.62 C |
| ATOM | 954 | OD1 | ASP | 121 | 28.013 | 17.411 | 50.189 | 1.00 | 42.25 O |
| ATOM | 955 | OD2 | ASP | 121 | 28.531 | 18.568 | 48.392 | 1.00 | 41.57 O |
| ATOM | 956 | C | ASP | 121 | 31.801 | 16.030 | 47.461 | 1.00 | 25.21 C |
| ATOM | 957 | O | ASP | 121 | 32.884 | 16.627 | 47.414 | 1.00 | 24.52 O |
| ATOM | 958 | N | VAL | 122 | 31.700 | 14.705 | 47.424 | 1.00 | 22.72 N |
| ATOM | 959 | CA | VAL | 122 | 32.876 | 13.859 | 47.326 | 1.00 | 23.61 C |
| ATOM | 960 | CB | VAL | 122 | 32.501 | 12.365 | 47.473 | 1.00 | 23.21 C |
| ATOM | 961 | CG1 | VAL | 122 | 33.729 | 11.499 | 47.241 | 1.00 | 22.69 C |
| ATOM | 962 | CG2 | VAL | 122 | 31.929 | 12.106 | 48.862 | 1.00 | 24.86 C |
| ATOM | 963 | C | VAL | 122 | 33.599 | 14.060 | 45.995 | 1.00 | 23.75 C |
| ATOM | 964 | O | VAL | 122 | 34.817 | 14.229 | 45.962 | 1.00 | 24.33 O |
| ATOM | 965 | N | MET | 123 | 32.847 | 14.036 | 44.901 | 1.00 | 25.05 N |
| ATOM | 966 | CA | MET | 123 | 33.426 | 14.212 | 43.571 | 1.00 | 25.29 C |
| ATOM | 967 | CB | MET | 123 | 32.338 | 14.206 | 42.503 | 1.00 | 25.78 C |
| ATOM | 968 | CG | MET | 123 | 31.662 | 12.894 | 42.275 | 1.00 | 27.47 C |
| ATOM | 969 | SD | MET | 123 | 30.635 | 13.039 | 40.826 | 1.00 | 25.52 S |
| ATOM | 970 | CE | MET | 123 | 29.038 | 13.408 | 41.522 | 1.00 | 25.19 C |
| ATOM | 971 | C | MET | 123 | 34.153 | 15.540 | 43.472 | 1.00 | 25.03 C |
| ATOM | 972 | O | MET | 123 | 35.328 | 15.606 | 43.118 | 1.00 | 22.07 O |
| ATOM | 973 | N | CYS | 124 | 33.417 | 16.603 | 43.769 | 1.00 | 25.57 N |
| ATOM | 974 | CA | CYS | 124 | 33.957 | 17.947 | 43.709 | 1.00 | 25.21 C |
| ATOM | 975 | C | CYS | 124 | 35.196 | 18.147 | 44.547 | 1.00 | 25.46 C |
| ATOM | 976 | O | CYS | 124 | 36.124 | 18.850 | 44.142 | 1.00 | 25.74 O |
| ATOM | 977 | CB | CYS | 124 | 32.890 | 18.943 | 44.131 | 1.00 | 24.57 C |
| ATOM | 978 | SG | CYS | 124 | 31.720 | 19.279 | 42.796 | 1.00 | 26.71 S |
| ATOM | 979 | N | THR | 125 | 35.207 | 17.536 | 45.724 | 1.00 | 25.24 N |
| ATOM | 980 | CA | THR | 125 | 36.343 | 17.653 | 46.614 | 1.00 | 24.06 C |
| ATOM | 981 | CB | THR | 125 | 35.998 | 17.118 | 48.009 | 1.00 | 25.11 C |
| ATOM | 982 | OG1 | THR | 125 | 34.961 | 17.927 | 48.574 | 1.00 | 25.31 O |
| ATOM | 983 | CG2 | THR | 125 | 37.209 | 17.155 | 48.917 | 1.00 | 26.39 C |
| ATOM | 984 | C | THR | 125 | 37.536 | 16.897 | 46.051 | 1.00 | 24.49 C |
| ATOM | 985 | O | THR | 125 | 38.669 | 17.367 | 46.128 | 1.00 | 24.80 O |
| ATOM | 986 | N | ALA | 126 | 37.279 | 15.728 | 45.475 | 1.00 | 23.51 N |
| ATOM | 987 | CA | ALA | 126 | 38.353 | 14.937 | 44.901 | 1.00 | 23.39 C |
| ATOM | 988 | CB | ALA | 126 | 37.825 | 13.576 | 44.452 | 1.00 | 25.21 C |
| ATOM | 989 | C | ALA | 126 | 38.895 | 15.719 | 43.713 | 1.00 | 23.10 C |
| ATOM | 990 | O | ALA | 126 | 40.104 | 15.818 | 43.526 | 1.00 | 22.38 O |
| ATOM | 991 | N | PHE | 127 | 37.982 | 16.281 | 42.925 | 1.00 | 23.88 N |
| ATOM | 992 | CA | PHE | 127 | 38.336 | 17.074 | 41.757 | 1.00 | 26.00 C |
| ATOM | 993 | CB | PHE | 127 | 37.063 | 17.649 | 41.118 | 1.00 | 26.05 C |
| ATOM | 994 | CG | PHE | 127 | 37.319 | 18.511 | 39.915 | 1.00 | 28.05 C |
| ATOM | 995 | CD1 | PHE | 127 | 37.759 | 17.951 | 38.718 | 1.00 | 29.22 C |
| ATOM | 996 | CD2 | PHE | 127 | 37.142 | 19.888 | 39.984 | 1.00 | 28.78 C |
| ATOM | 997 | CE1 | PHE | 127 | 38.020 | 18.752 | 37.607 | 1.00 | 27.59 C |
| ATOM | 998 | CE2 | PHE | 127 | 37.400 | 20.700 | 38.881 | 1.00 | 29.70 C |
| ATOM | 999 | CZ | PHE | 127 | 37.841 | 20.128 | 37.688 | 1.00 | 29.75 C |
| ATOM | 1000 | C | PHE | 127 | 39.270 | 18.205 | 42.178 | 1.00 | 27.81 C |
| ATOM | 1001 | O | PHE | 127 | 40.319 | 18.426 | 41.567 | 1.00 | 25.51 O |
| ATOM | 1002 | N | HIS | 128 | 38.885 | 18.911 | 43.237 | 1.00 | 28.91 N |
| ATOM | 1003 | CA | HIS | 128 | 39.675 | 20.026 | 43.752 | 1.00 | 30.38 C |
| ATOM | 1004 | CB | HIS | 128 | 38.920 | 20.740 | 44.877 | 1.00 | 32.39 C |
| ATOM | 1005 | CG | HIS | 128 | 39.721 | 21.811 | 45.549 | 1.00 | 35.91 C |
| ATOM | 1006 | CD2 | HIS | 128 | 40.401 | 21.813 | 46.720 | 1.00 | 37.04 C |
| ATOM | 1007 | ND1 | HIS | 128 | 39.936 | 23.049 | 44.980 | 1.00 | 37.93 N |
| ATOM | 1008 | CE1 | HIS | 128 | 40.714 | 23.766 | 45.771 | 1.00 | 37.78 C |
| ATOM | 1009 | NE2 | HIS | 128 | 41.010 | 23.039 | 46.834 | 1.00 | 36.51 N |
| ATOM | 1010 | C | HIS | 128 | 41.040 | 19.618 | 44.280 | 1.00 | 30.75 C |
| ATOM | 1011 | O | HIS | 128 | 42.036 | 20.294 | 44.028 | 1.00 | 30.33 O |
| ATOM | 1012 | N | ASP | 129 | 41.090 | 18.523 | 45.030 | 1.00 | 31.65 N |
| ATOM | 1013 | CA | ASP | 129 | 42.356 | 18.075 | 45.596 | 1.00 | 33.00 C |
| ATOM | 1014 | CB | ASP | 129 | 42.130 | 16.891 | 46.544 | 1.00 | 34.16 C |
| ATOM | 1015 | CG | ASP | 129 | 41.220 | 17.242 | 47.710 | 1.00 | 36.93 C |
| ATOM | 1016 | OD1 | ASP | 129 | 41.162 | 18.433 | 48.088 | 1.00 | 37.00 O |
| ATOM | 1017 | OD2 | ASP | 129 | 40.573 | 16.324 | 48.258 | 1.00 | 38.07 O |
| ATOM | 1018 | C | ASP | 129 | 43.380 | 17.701 | 44.529 | 1.00 | 33.92 C |
| ATOM | 1019 | O | ASP | 129 | 44.585 | 17.862 | 44.730 | 1.00 | 33.33 O |
| ATOM | 1020 | N | ASN | 130 | 42.903 | 17.199 | 43.394 | 1.00 | 34.53 N |
| ATOM | 1021 | CA | ASN | 130 | 43.803 | 16.819 | 42.312 | 1.00 | 34.04 C |
| ATOM | 1022 | CB | ASN | 130 | 44.645 | 15.612 | 42.728 | 1.00 | 36.13 C |
| ATOM | 1023 | CG | ASN | 130 | 45.770 | 15.316 | 41.746 | 1.00 | 39.82 C |
| ATOM | 1024 | OD1 | ASN | 130 | 46.644 | 14.497 | 42.022 | 1.00 | 43.50 O |
| ATOM | 1025 | ND2 | ASN | 130 | 45.748 | 15.978 | 40.594 | 1.00 | 38.81 N |
| ATOM | 1026 | C | ASN | 130 | 43.024 | 16.503 | 41.045 | 1.00 | 32.63 C |

-continued

| ATOM | 1027 | O   | ASN | 130 | 42.692 | 15.348 | 40.778 | 1.00 | 31.11 | O |
| ---- | ---- | --- | --- | --- | ------ | ------ | ------ | ---- | ----- | - |
| ATOM | 1028 | N   | GLU | 131 | 42.739 | 17.546 | 40.275 | 1.00 | 30.08 | N |
| ATOM | 1029 | CA  | GLU | 131 | 41.997 | 17.424 | 39.026 | 1.00 | 32.21 | C |
| ATOM | 1030 | CB  | GLU | 131 | 41.879 | 18.790 | 38.346 | 1.00 | 33.42 | C |
| ATOM | 1031 | CG  | GLU | 131 | 40.899 | 19.737 | 39.001 | 1.00 | 39.40 | C |
| ATOM | 1032 | CD  | GLU | 131 | 40.958 | 21.134 | 38.412 | 1.00 | 41.82 | C |
| ATOM | 1033 | OE1 | GLU | 131 | 41.060 | 21.256 | 37.171 | 1.00 | 42.45 | O |
| ATOM | 1034 | OE2 | GLU | 131 | 40.890 | 22.108 | 39.195 | 1.00 | 43.51 | O |
| ATOM | 1035 | C   | GLU | 131 | 42.647 | 16.455 | 38.051 | 1.00 | 30.48 | C |
| ATOM | 1036 | O   | GLU | 131 | 41.965 | 15.652 | 37.415 | 1.00 | 28.19 | O |
| ATOM | 1037 | N   | GLU | 132 | 43.966 | 16.552 | 37.928 | 1.00 | 30.36 | N |
| ATOM | 1038 | CA  | GLU | 132 | 44.720 | 15.702 | 37.013 | 1.00 | 30.68 | C |
| ATOM | 1039 | CB  | GLU | 132 | 46.219 | 15.971 | 37.157 | 1.00 | 34.57 | C |
| ATOM | 1040 | CG  | GLU | 132 | 46.612 | 17.440 | 37.283 | 1.00 | 41.76 | C |
| ATOM | 1041 | CD  | GLU | 132 | 46.367 | 18.243 | 36.018 | 1.00 | 45.66 | C |
| ATOM | 1042 | OE1 | GLU | 132 | 46.935 | 19.351 | 35.910 | 1.00 | 48.52 | O |
| ATOM | 1043 | OE2 | GLU | 132 | 45.609 | 17.776 | 35.138 | 1.00 | 48.47 | O |
| ATOM | 1044 | C   | GLU | 132 | 44.460 | 14.230 | 37.289 | 1.00 | 28.06 | C |
| ATOM | 1045 | O   | GLU | 132 | 43.965 | 13.502 | 36.430 | 1.00 | 27.02 | O |
| ATOM | 1046 | N   | THR | 133 | 44.807 | 13.798 | 38.496 | 1.00 | 25.26 | N |
| ATOM | 1047 | CA  | THR | 133 | 44.635 | 12.408 | 38.903 | 1.00 | 23.70 | C |
| ATOM | 1048 | CB  | THR | 133 | 45.224 | 12.176 | 40.313 | 1.00 | 25.41 | C |
| ATOM | 1049 | OG1 | THR | 133 | 46.634 | 12.426 | 40.277 | 1.00 | 27.80 | O |
| ATOM | 1050 | CG2 | THR | 133 | 44.973 | 10.741 | 40.785 | 1.00 | 24.34 | C |
| ATOM | 1051 | C   | THR | 133 | 43.176 | 11.974 | 38.895 | 1.00 | 23.48 | C |
| ATOM | 1052 | O   | THR | 133 | 42.854 | 10.867 | 38.470 | 1.00 | 22.17 | O |
| ATOM | 1053 | N   | PHE | 134 | 42.300 | 12.851 | 39.372 | 1.00 | 21.62 | N |
| ATOM | 1054 | CA  | PHE | 134 | 40.874 | 12.568 | 39.420 | 1.00 | 22.13 | C |
| ATOM | 1055 | CB  | PHE | 134 | 40.128 | 13.788 | 39.966 | 1.00 | 22.53 | C |
| ATOM | 1056 | CG  | PHE | 134 | 38.638 | 13.625 | 40.000 | 1.00 | 22.38 | C |
| ATOM | 1057 | CD1 | PHE | 134 | 38.039 | 12.760 | 40.908 | 1.00 | 22.96 | C |
| ATOM | 1058 | CD2 | PHE | 134 | 37.834 | 14.325 | 39.113 | 1.00 | 21.91 | C |
| ATOM | 1059 | CE1 | PHE | 134 | 36.661 | 12.598 | 40.929 | 1.00 | 22.17 | C |
| ATOM | 1060 | CE2 | PHE | 134 | 36.459 | 14.171 | 39.124 | 1.00 | 20.58 | C |
| ATOM | 1061 | CZ  | PHE | 134 | 35.868 | 13.307 | 40.034 | 1.00 | 22.88 | C |
| ATOM | 1062 | C   | PHE | 134 | 40.363 | 12.232 | 38.018 | 1.00 | 21.41 | C |
| ATOM | 1063 | O   | PHE | 134 | 39.693 | 11.216 | 37.813 | 1.00 | 22.84 | O |
| ATOM | 1064 | N   | LEU | 135 | 40.690 | 13.101 | 37.068 | 1.00 | 20.12 | N |
| ATOM | 1065 | CA  | LEU | 135 | 40.292 | 12.945 | 35.672 | 1.00 | 22.65 | C |
| ATOM | 1066 | CB  | LEU | 135 | 40.600 | 14.231 | 34.899 | 1.00 | 23.79 | C |
| ATOM | 1067 | CG  | LEU | 135 | 39.478 | 15.225 | 34.575 | 1.00 | 26.03 | C |
| ATOM | 1068 | CD1 | LEU | 135 | 38.372 | 15.137 | 35.586 | 1.00 | 25.72 | C |
| ATOM | 1069 | CD2 | LEU | 135 | 40.068 | 16.633 | 34.504 | 1.00 | 23.26 | C |
| ATOM | 1070 | C   | LEU | 135 | 40.981 | 11.767 | 34.990 | 1.00 | 21.48 | C |
| ATOM | 1071 | O   | LEU | 135 | 40.337 | 10.976 | 34.307 | 1.00 | 20.90 | O |
| ATOM | 1072 | N   | LYS | 136 | 42.292 | 11.652 | 35.161 | 1.00 | 22.49 | N |
| ATOM | 1073 | CA  | LYS | 136 | 43.007 | 10.554 | 34.530 | 1.00 | 21.84 | C |
| ATOM | 1074 | CB  | LYS | 136 | 44.519 | 10.740 | 34.679 | 1.00 | 24.08 | C |
| ATOM | 1075 | CG  | LYS | 136 | 45.064 | 12.011 | 34.030 | 1.00 | 28.34 | C |
| ATOM | 1076 | CD  | LYS | 136 | 44.423 | 12.287 | 32.670 | 1.00 | 33.82 | C |
| ATOM | 1077 | CE  | LYS | 136 | 44.772 | 13.685 | 32.158 | 1.00 | 35.73 | C |
| ATOM | 1078 | NZ  | LYS | 136 | 43.909 | 14.108 | 31.012 | 1.00 | 37.92 | N |
| ATOM | 1079 | C   | LYS | 136 | 42.558 | 9.214  | 35.118 | 1.00 | 21.60 | C |
| ATOM | 1080 | O   | LYS | 136 | 42.430 | 8.227  | 34.398 | 1.00 | 20.22 | O |
| ATOM | 1081 | N   | LYS | 137 | 42.306 | 9.189  | 36.423 | 1.00 | 18.95 | N |
| ATOM | 1082 | CA  | LYS | 137 | 41.852 | 7.974  | 37.090 | 1.00 | 21.28 | C |
| ATOM | 1083 | CB  | LYS | 137 | 41.544 | 8.273  | 38.562 | 1.00 | 25.63 | C |
| ATOM | 1084 | CG  | LYS | 137 | 41.269 | 7.050  | 39.426 | 1.00 | 31.71 | C |
| ATOM | 1085 | CD  | LYS | 137 | 42.537 | 6.254  | 39.686 | 1.00 | 35.51 | C |
| ATOM | 1086 | CE  | LYS | 137 | 42.304 | 5.152  | 40.715 | 1.00 | 38.22 | C |
| ATOM | 1087 | NZ  | LYS | 137 | 41.271 | 4.180  | 40.265 | 1.00 | 40.14 | N |
| ATOM | 1088 | C   | LYS | 137 | 40.598 | 7.438  | 36.392 | 1.00 | 20.35 | C |
| ATOM | 1089 | O   | LYS | 137 | 40.521 | 6.256  | 36.058 | 1.00 | 20.90 | O |
| ATOM | 1090 | N   | TYR | 138 | 39.615 | 8.308  | 36.170 | 1.00 | 20.99 | N |
| ATOM | 1091 | CA  | TYR | 138 | 38.389 | 7.891  | 35.504 | 1.00 | 19.67 | C |
| ATOM | 1092 | CB  | TYR | 138 | 37.304 | 8.954  | 35.669 | 1.00 | 23.50 | C |
| ATOM | 1093 | CG  | TYR | 138 | 36.562 | 8.834  | 36.982 | 1.00 | 26.68 | C |
| ATOM | 1094 | CD1 | TYR | 138 | 36.955 | 9.562  | 38.109 | 1.00 | 28.98 | C |
| ATOM | 1095 | CE1 | TYR | 138 | 36.274 | 9.429  | 39.325 | 1.00 | 30.78 | C |
| ATOM | 1096 | CD2 | TYR | 138 | 35.478 | 7.970  | 37.103 | 1.00 | 27.96 | C |
| ATOM | 1097 | CE2 | TYR | 138 | 34.797 | 7.826  | 38.307 | 1.00 | 29.85 | C |
| ATOM | 1098 | CZ  | TYR | 138 | 35.195 | 8.553  | 39.411 | 1.00 | 32.30 | C |
| ATOM | 1099 | OH  | TYR | 138 | 34.513 | 8.389  | 40.594 | 1.00 | 32.94 | O |
| ATOM | 1100 | C   | TYR | 138 | 38.602 | 7.563  | 34.027 | 1.00 | 19.85 | C |
| ATOM | 1101 | O   | TYR | 138 | 37.943 | 6.676  | 33.477 | 1.00 | 18.93 | O |
| ATOM | 1102 | N   | LEU | 139 | 39.522 | 8.277  | 33.386 | 1.00 | 19.83 | N |
| ATOM | 1103 | CA  | LEU | 139 | 39.828 | 8.022  | 31.983 | 1.00 | 19.04 | C |
| ATOM | 1104 | CB  | LEU | 139 | 40.925 | 8.977  | 31.504 | 1.00 | 17.82 | C |
| ATOM | 1105 | CG  | LEU | 139 | 41.430 | 8.814  | 30.065 | 1.00 | 19.51 | C |

| | | | | -continued | | | | | |
|---|---|---|---|---|---|---|---|---|---|
| ATOM | 1106 | CD1 | LEU | 139 | 40.252 | 8.806 | 29.088 | 1.00 | 20.02 | C |
| ATOM | 1107 | CD2 | LEU | 139 | 42.399 | 9.941 | 29.740 | 1.00 | 19.89 | C |
| ATOM | 1108 | C | LEU | 139 | 40.309 | 6.574 | 31.898 | 1.00 | 18.34 | C |
| ATOM | 1109 | O | LEU | 139 | 39.940 | 5.827 | 30.991 | 1.00 | 18.31 | O |
| ATOM | 1110 | N | TYR | 140 | 41.125 | 6.185 | 32.872 | 1.00 | 17.67 | N |
| ATOM | 1111 | CA | TYR | 140 | 41.660 | 4.830 | 32.950 | 1.00 | 17.75 | C |
| ATOM | 1112 | CB | TYR | 140 | 42.751 | 4.787 | 34.039 | 1.00 | 17.17 | C |
| ATOM | 1113 | CG | TYR | 140 | 42.900 | 3.472 | 34.770 | 1.00 | 18.96 | C |
| ATOM | 1114 | CD1 | TYR | 140 | 42.179 | 3.220 | 35.933 | 1.00 | 16.92 | C |
| ATOM | 1115 | CE1 | TYR | 140 | 42.309 | 2.017 | 36.614 | 1.00 | 19.26 | C |
| ATOM | 1116 | CD2 | TYR | 140 | 43.764 | 2.482 | 34.301 | 1.00 | 17.81 | C |
| ATOM | 1117 | CE2 | TYR | 140 | 43.902 | 1.276 | 34.976 | 1.00 | 19.95 | C |
| ATOM | 1118 | CZ | TYR | 140 | 43.170 | 1.051 | 36.131 | 1.00 | 18.94 | C |
| ATOM | 1119 | OH | TYR | 140 | 43.282 | −0.143 | 36.793 | 1.00 | 19.16 | O |
| ATOM | 1120 | C | TYR | 140 | 40.554 | 3.802 | 33.225 | 1.00 | 17.59 | C |
| ATOM | 1121 | O | TYR | 140 | 40.525 | 2.734 | 32.615 | 1.00 | 17.88 | O |
| ATOM | 1122 | N | GLU | 141 | 39.633 | 4.131 | 34.124 | 1.00 | 16.76 | N |
| ATOM | 1123 | CA | GLU | 141 | 38.544 | 3.213 | 34.464 | 1.00 | 17.55 | C |
| ATOM | 1124 | CB | GLU | 141 | 37.711 | 3.770 | 35.625 | 1.00 | 18.26 | C |
| ATOM | 1125 | CG | GLU | 141 | 38.487 | 4.002 | 36.914 | 1.00 | 20.55 | C |
| ATOM | 1126 | CD | GLU | 141 | 38.836 | 2.718 | 37.653 | 1.00 | 20.42 | C |
| ATOM | 1127 | OE1 | GLU | 141 | 38.589 | 1.614 | 37.127 | 1.00 | 22.10 | O |
| ATOM | 1128 | OE2 | GLU | 141 | 39.372 | 2.819 | 38.773 | 1.00 | 23.02 | O |
| ATOM | 1129 | C | GLU | 141 | 37.630 | 2.955 | 33.269 | 1.00 | 17.54 | C |
| ATOM | 1130 | O | GLU | 141 | 37.163 | 1.832 | 33.048 | 1.00 | 15.35 | O |
| ATOM | 1131 | N | ILE | 142 | 37.376 | 3.996 | 32.489 | 1.00 | 17.68 | N |
| ATOM | 1132 | CA | ILE | 142 | 36.508 | 3.851 | 31.329 | 1.00 | 18.05 | C |
| ATOM | 1133 | CB | ILE | 142 | 36.002 | 5.227 | 30.836 | 1.00 | 16.78 | C |
| ATOM | 1134 | CG2 | ILE | 142 | 35.323 | 5.091 | 29.474 | 1.00 | 18.86 | C |
| ATOM | 1135 | CG1 | ILE | 142 | 34.983 | 5.780 | 31.832 | 1.00 | 17.88 | C |
| ATOM | 1136 | CD1 | ILE | 142 | 33.767 | 4.879 | 32.000 | 1.00 | 19.63 | C |
| ATOM | 1137 | C | ILE | 142 | 37.217 | 3.134 | 30.193 | 1.00 | 17.02 | C |
| ATOM | 1138 | O | ILE | 142 | 36.639 | 2.262 | 29.547 | 1.00 | 17.44 | O |
| ATOM | 1139 | N | ALA | 143 | 38.466 | 3.513 | 29.946 | 1.00 | 17.64 | N |
| ATOM | 1140 | CA | ALA | 143 | 39.251 | 2.907 | 28.877 | 1.00 | 19.82 | C |
| ATOM | 1141 | CB | ALA | 143 | 40.641 | 3.552 | 28.811 | 1.00 | 18.81 | C |
| ATOM | 1142 | C | ALA | 143 | 39.391 | 1.396 | 29.057 | 1.00 | 20.58 | C |
| ATOM | 1143 | O | ALA | 143 | 39.113 | 0.633 | 28.136 | 1.00 | 22.08 | O |
| ATOM | 1144 | N | ARG | 144 | 39.814 | 0.959 | 30.239 | 1.00 | 20.57 | N |
| ATOM | 1145 | CA | ARG | 144 | 39.990 | −0.471 | 30.457 | 1.00 | 21.41 | C |
| ATOM | 1146 | CB | ARG | 144 | 40.738 | −0.726 | 31.763 | 1.00 | 20.26 | C |
| ATOM | 1147 | CG | ARG | 144 | 39.956 | −0.441 | 33.034 | 1.00 | 22.71 | C |
| ATOM | 1148 | CD | ARG | 144 | 40.912 | −0.524 | 34.208 | 1.00 | 23.88 | C |
| ATOM | 1149 | NE | ARG | 144 | 40.244 | −0.438 | 35.498 | 1.00 | 27.58 | N |
| ATOM | 1150 | CZ | ARG | 144 | 40.340 | −1.371 | 36.441 | 1.00 | 29.71 | C |
| ATOM | 1151 | NH1 | ARG | 144 | 39.705 | −1.217 | 37.596 | 1.00 | 30.74 | N |
| ATOM | 1152 | NH2 | ARG | 144 | 41.062 | −2.462 | 36.226 | 1.00 | 29.23 | N |
| ATOM | 1153 | C | ARG | 144 | 38.679 | −1.257 | 30.432 | 1.00 | 20.40 | C |
| ATOM | 1154 | O | ARG | 144 | 38.686 | −2.467 | 30.235 | 1.00 | 23.27 | O |
| ATOM | 1155 | N | ARG | 145 | 37.558 | −0.573 | 30.634 | 1.00 | 20.53 | N |
| ATOM | 1156 | CA | ARG | 145 | 36.250 | −1.223 | 30.604 | 1.00 | 21.62 | C |
| ATOM | 1157 | CB | ARG | 145 | 35.250 | −0.499 | 31.507 | 1.00 | 21.06 | C |
| ATOM | 1158 | CG | ARG | 145 | 35.400 | −0.802 | 32.973 | 1.00 | 23.28 | C |
| ATOM | 1159 | CD | ARG | 145 | 34.334 | −0.078 | 33.780 | 1.00 | 23.01 | C |
| ATOM | 1160 | NE | ARG | 145 | 34.398 | −0.443 | 35.189 | 1.00 | 23.19 | N |
| ATOM | 1161 | CZ | ARG | 145 | 35.425 | −0.165 | 35.982 | 1.00 | 26.04 | C |
| ATOM | 1162 | NH1 | ARG | 145 | 35.399 | −0.535 | 37.252 | 1.00 | 23.21 | N |
| ATOM | 1163 | NH2 | ARG | 145 | 36.482 | 0.487 | 35.502 | 1.00 | 24.21 | N |
| ATOM | 1164 | C | ARG | 145 | 35.711 | −1.209 | 29.187 | 1.00 | 22.10 | C |
| ATOM | 1165 | O | ARG | 145 | 34.767 | −1.931 | 28.862 | 1.00 | 21.98 | O |
| ATOM | 1166 | N | HIS | 146 | 36.304 | −0.364 | 28.352 | 1.00 | 20.74 | N |
| ATOM | 1167 | CA | HIS | 146 | 35.883 | −0.252 | 26.975 | 1.00 | 21.51 | C |
| ATOM | 1168 | CB | HIS | 146 | 35.041 | 1.007 | 26.781 | 1.00 | 22.50 | C |
| ATOM | 1169 | CG | HIS | 146 | 33.792 | 1.010 | 27.598 | 1.00 | 22.49 | C |
| ATOM | 1170 | CD2 | HIS | 146 | 32.540 | 0.588 | 27.309 | 1.00 | 22.56 | C |
| ATOM | 1171 | ND1 | HIS | 146 | 33.771 | 1.401 | 28.919 | 1.00 | 24.88 | N |
| ATOM | 1172 | CE1 | HIS | 146 | 32.560 | 1.216 | 29.410 | 1.00 | 22.26 | C |
| ATOM | 1173 | NE2 | HIS | 146 | 31.794 | 0.722 | 28.453 | 1.00 | 26.94 | N |
| ATOM | 1174 | C | HIS | 146 | 37.037 | −0.260 | 25.995 | 1.00 | 24.46 | C |
| ATOM | 1175 | O | HIS | 146 | 37.323 | 0.744 | 25.338 | 1.00 | 25.17 | O |
| ATOM | 1176 | N | PRO | 147 | 37.744 | −1.392 | 25.904 | 1.00 | 26.06 | N |
| ATOM | 1177 | CD | PRO | 147 | 37.460 | −2.737 | 26.437 | 1.00 | 24.64 | C |
| ATOM | 1178 | CA | PRO | 147 | 38.851 | −1.419 | 24.951 | 1.00 | 28.42 | C |
| ATOM | 1179 | CB | PRO | 147 | 39.485 | −2.776 | 25.218 | 1.00 | 27.61 | C |
| ATOM | 1180 | CG | PRO | 147 | 38.280 | −3.633 | 25.526 | 1.00 | 25.89 | C |
| ATOM | 1181 | C | PRO | 147 | 38.085 | −1.374 | 23.636 | 1.00 | 30.98 | C |
| ATOM | 1182 | O | PRO | 147 | 37.006 | −1.947 | 23.549 | 1.00 | 36.58 | O |
| ATOM | 1183 | N | TYR | 148 | 38.615 | −0.688 | 22.638 | 1.00 | 32.85 | N |
| ATOM | 1184 | CA | TYR | 148 | 37.954 | −0.545 | 21.334 | 1.00 | 29.99 | C |

-continued

| | | | | | | | | |
|---|---|---|---|---|---|---|---|---|
| ATOM | 1185 | CB | TYR | 148 | 36.941 | −1.675 | 21.054 | 1.00 | 33.17 | C |
| ATOM | 1186 | CG | TYR | 148 | 37.557 | −3.053 | 20.939 | 1.00 | 35.18 | C |
| ATOM | 1187 | CD1 | TYR | 148 | 38.635 | −3.291 | 20.085 | 1.00 | 36.97 | C |
| ATOM | 1188 | CE1 | TYR | 148 | 39.216 | −4.555 | 19.996 | 1.00 | 38.30 | C |
| ATOM | 1189 | CD2 | TYR | 148 | 37.072 | −4.116 | 21.698 | 1.00 | 36.29 | C |
| ATOM | 1190 | CE2 | TYR | 148 | 37.643 | −5.378 | 21.617 | 1.00 | 36.22 | C |
| ATOM | 1191 | CZ | TYR | 148 | 38.712 | −5.592 | 20.769 | 1.00 | 37.87 | C |
| ATOM | 1192 | OH | TYR | 148 | 39.282 | −6.843 | 20.711 | 1.00 | 39.48 | O |
| ATOM | 1193 | C | TYR | 148 | 37.251 | 0.803 | 21.237 | 1.00 | 27.72 | C |
| ATOM | 1194 | O | TYR | 148 | 36.952 | 1.262 | 20.138 | 1.00 | 26.55 | O |
| ATOM | 1195 | N | PHE | 149 | 36.974 | 1.439 | 22.375 | 1.00 | 24.34 | N |
| ATOM | 1196 | CA | PHE | 149 | 36.345 | 2.761 | 22.340 | 1.00 | 21.61 | C |
| ATOM | 1197 | CB | PHE | 149 | 35.929 | 3.210 | 23.745 | 1.00 | 20.84 | C |
| ATOM | 1198 | CG | PHE | 149 | 34.976 | 4.382 | 23.760 | 1.00 | 21.56 | C |
| ATOM | 1199 | CD1 | PHE | 149 | 35.361 | 5.625 | 23.262 | 1.00 | 22.58 | C |
| ATOM | 1200 | CD2 | PHE | 149 | 33.689 | 4.238 | 24.272 | 1.00 | 24.69 | C |
| ATOM | 1201 | CE1 | PHE | 149 | 34.482 | 6.705 | 23.274 | 1.00 | 23.37 | C |
| ATOM | 1202 | CE2 | PHE | 149 | 32.796 | 5.314 | 24.288 | 1.00 | 21.99 | C |
| ATOM | 1203 | CZ | PHE | 149 | 33.195 | 6.548 | 23.789 | 1.00 | 25.70 | C |
| ATOM | 1204 | C | PHE | 149 | 37.458 | 3.661 | 21.796 | 1.00 | 20.57 | C |
| ATOM | 1205 | O | PHE | 149 | 38.537 | 3.744 | 22.382 | 1.00 | 18.38 | O |
| ATOM | 1206 | N | TYR | 150 | 37.202 | 4.307 | 20.664 | 1.00 | 18.85 | N |
| ATOM | 1207 | CA | TYR | 150 | 38.191 | 5.173 | 20.023 | 1.00 | 19.13 | C |
| ATOM | 1208 | CB | TYR | 150 | 37.527 | 5.960 | 18.893 | 1.00 | 18.20 | C |
| ATOM | 1209 | CG | TYR | 150 | 38.509 | 6.627 | 17.963 | 1.00 | 17.36 | C |
| ATOM | 1210 | CD1 | TYR | 150 | 38.404 | 7.984 | 17.673 | 1.00 | 18.89 | C |
| ATOM | 1211 | CE1 | TYR | 150 | 39.339 | 8.621 | 16.850 | 1.00 | 18.93 | C |
| ATOM | 1212 | CD2 | TYR | 150 | 39.568 | 5.909 | 17.403 | 1.00 | 17.97 | C |
| ATOM | 1213 | CE2 | TYR | 150 | 40.510 | 6.537 | 16.578 | 1.00 | 19.15 | C |
| ATOM | 1214 | CZ | TYR | 150 | 40.387 | 7.892 | 16.312 | 1.00 | 19.04 | C |
| ATOM | 1215 | OH | TYR | 150 | 41.333 | 8.531 | 15.540 | 1.00 | 19.32 | O |
| ATOM | 1216 | C | TYR | 150 | 38.832 | 6.126 | 21.038 | 1.00 | 19.02 | C |
| ATOM | 1217 | O | TYR | 150 | 38.177 | 7.038 | 21.549 | 1.00 | 17.89 | O |
| ATOM | 1218 | N | ALA | 151 | 40.119 | 5.915 | 21.307 | 1.00 | 18.89 | N |
| ATOM | 1219 | CA | ALA | 151 | 40.855 | 6.712 | 22.289 | 1.00 | 18.55 | C |
| ATOM | 1220 | CB | ALA | 151 | 42.343 | 6.355 | 22.243 | 1.00 | 18.96 | C |
| ATOM | 1221 | C | ALA | 151 | 40.685 | 8.228 | 22.221 | 1.00 | 18.61 | C |
| ATOM | 1222 | O | ALA | 151 | 40.335 | 8.858 | 23.218 | 1.00 | 17.01 | O |
| ATOM | 1223 | N | PRO | 152 | 40.939 | 8.836 | 21.054 | 1.00 | 20.09 | N |
| ATOM | 1224 | CD | PRO | 152 | 41.443 | 8.266 | 19.791 | 1.00 | 20.43 | C |
| ATOM | 1225 | CA | PRO | 152 | 40.794 | 10.289 | 20.941 | 1.00 | 18.74 | C |
| ATOM | 1226 | CB | PRO | 152 | 41.043 | 10.542 | 19.457 | 1.00 | 20.71 | C |
| ATOM | 1227 | CG | PRO | 152 | 42.032 | 9.484 | 19.109 | 1.00 | 18.05 | C |
| ATOM | 1228 | C | PRO | 152 | 39.423 | 10.767 | 21.386 | 1.00 | 19.54 | C |
| ATOM | 1229 | O | PRO | 152 | 39.290 | 11.819 | 22.016 | 1.00 | 17.71 | O |
| ATOM | 1230 | N | GLU | 153 | 38.401 | 9.977 | 21.075 | 1.00 | 19.85 | N |
| ATOM | 1231 | CA | GLU | 153 | 37.055 | 10.359 | 21.444 | 1.00 | 21.95 | C |
| ATOM | 1232 | CB | GLU | 153 | 36.033 | 9.387 | 20.849 | 1.00 | 24.96 | C |
| ATOM | 1233 | CG | GLU | 153 | 34.650 | 9.992 | 20.756 | 1.00 | 31.24 | C |
| ATOM | 1234 | CD | GLU | 153 | 33.597 | 8.991 | 20.348 | 1.00 | 35.06 | C |
| ATOM | 1235 | OE1 | GLU | 153 | 33.846 | 8.211 | 19.403 | 1.00 | 38.93 | O |
| ATOM | 1236 | OE2 | GLU | 153 | 32.515 | 8.994 | 20.969 | 1.00 | 36.93 | O |
| ATOM | 1237 | C | GLU | 153 | 36.922 | 10.411 | 22.961 | 1.00 | 20.85 | C |
| ATOM | 1238 | O | GLU | 153 | 36.189 | 11.239 | 23.492 | 1.00 | 18.84 | O |
| ATOM | 1239 | N | LEU | 154 | 37.629 | 9.534 | 23.667 | 1.00 | 20.47 | N |
| ATOM | 1240 | CA | LEU | 154 | 37.568 | 9.559 | 25.126 | 1.00 | 20.34 | C |
| ATOM | 1241 | CB | LEU | 154 | 38.336 | 8.383 | 25.720 | 1.00 | 20.20 | C |
| ATOM | 1242 | CG | LEU | 154 | 37.714 | 7.010 | 25.482 | 1.00 | 18.80 | C |
| ATOM | 1243 | CD1 | LEU | 154 | 38.639 | 5.932 | 26.025 | 1.00 | 20.39 | C |
| ATOM | 1244 | CD2 | LEU | 154 | 36.357 | 6.939 | 26.166 | 1.00 | 19.78 | C |
| ATOM | 1245 | C | LEU | 154 | 38.160 | 10.866 | 25.637 | 1.00 | 20.24 | C |
| ATOM | 1246 | O | LEU | 154 | 37.769 | 11.366 | 26.684 | 1.00 | 19.41 | O |
| ATOM | 1247 | N | LEU | 155 | 39.103 | 11.420 | 24.884 | 1.00 | 21.90 | N |
| ATOM | 1248 | CA | LEU | 155 | 39.740 | 12.677 | 25.261 | 1.00 | 24.33 | C |
| ATOM | 1249 | CB | LEU | 155 | 40.936 | 12.946 | 24.348 | 1.00 | 27.49 | C |
| ATOM | 1250 | CG | LEU | 155 | 42.301 | 12.999 | 25.035 | 1.00 | 30.37 | C |
| ATOM | 1251 | CD1 | LEU | 155 | 42.503 | 11.765 | 25.902 | 1.00 | 29.59 | C |
| ATOM | 1252 | CD2 | LEU | 155 | 43.387 | 13.106 | 23.975 | 1.00 | 29.50 | C |
| ATOM | 1253 | C | LEU | 155 | 38.743 | 13.829 | 25.168 | 1.00 | 24.16 | C |
| ATOM | 1254 | O | LEU | 155 | 38.797 | 14.785 | 25.953 | 1.00 | 22.95 | O |
| ATOM | 1255 | N | PHE | 156 | 37.836 | 13.743 | 24.201 | 1.00 | 22.87 | N |
| ATOM | 1256 | CA | PHE | 156 | 36.826 | 14.778 | 24.036 | 1.00 | 23.49 | C |
| ATOM | 1257 | CB | PHE | 156 | 36.090 | 14.589 | 22.708 | 1.00 | 25.45 | C |
| ATOM | 1258 | CG | PHE | 156 | 36.932 | 14.928 | 21.503 | 1.00 | 29.56 | C |
| ATOM | 1259 | CD1 | PHE | 156 | 37.151 | 16.255 | 21.144 | 1.00 | 31.82 | C |
| ATOM | 1260 | CD2 | PHE | 156 | 37.533 | 13.922 | 20.749 | 1.00 | 30.99 | C |
| ATOM | 1261 | CE1 | PHE | 156 | 37.960 | 16.577 | 20.050 | 1.00 | 33.40 | C |
| ATOM | 1262 | CE2 | PHE | 156 | 38.344 | 14.229 | 19.654 | 1.00 | 30.51 | C |
| ATOM | 1263 | CZ | PHE | 156 | 38.557 | 15.556 | 19.305 | 1.00 | 34.47 | C |

-continued

| | | | | | | | | | |
|---|---|---|---|---|---|---|---|---|---|
| ATOM | 1264 | C | PHE | 156 | 35.859 | 14.714 | 25.213 | 1.00 | 22.22 C |
| ATOM | 1265 | O | PHE | 156 | 35.474 | 15.738 | 25.759 | 1.00 | 22.45 O |
| ATOM | 1266 | N | PHE | 157 | 35.466 | 13.509 | 25.608 | 1.00 | 22.20 N |
| ATOM | 1267 | CA | PHE | 157 | 34.570 | 13.365 | 26.756 | 1.00 | 22.08 C |
| ATOM | 1268 | CB | PHE | 157 | 34.214 | 11.894 | 26.967 | 1.00 | 22.26 C |
| ATOM | 1269 | CG | PHE | 157 | 33.025 | 11.442 | 26.182 | 1.00 | 23.20 C |
| ATOM | 1270 | CD1 | PHE | 157 | 31.738 | 11.705 | 26.637 | 1.00 | 24.43 C |
| ATOM | 1271 | CD2 | PHE | 157 | 33.186 | 10.772 | 24.974 | 1.00 | 22.58 C |
| ATOM | 1272 | CE1 | PHE | 157 | 30.623 | 11.308 | 25.896 | 1.00 | 22.53 C |
| ATOM | 1273 | CE2 | PHE | 157 | 32.083 | 10.373 | 24.229 | 1.00 | 23.96 C |
| ATOM | 1274 | CZ | PHE | 157 | 30.799 | 10.642 | 24.690 | 1.00 | 24.03 C |
| ATOM | 1275 | C | PHE | 157 | 35.245 | 13.908 | 28.019 | 1.00 | 22.30 C |
| ATOM | 1276 | O | PHE | 157 | 34.629 | 14.625 | 28.810 | 1.00 | 21.71 O |
| ATOM | 1277 | N | ALA | 158 | 36.521 | 13.564 | 28.191 | 1.00 | 23.15 N |
| ATOM | 1278 | CA | ALA | 158 | 37.296 | 13.990 | 29.353 | 1.00 | 23.32 C |
| ATOM | 1279 | CB | ALA | 158 | 38.724 | 13.486 | 29.233 | 1.00 | 26.20 C |
| ATOM | 1280 | C | ALA | 158 | 37.295 | 15.497 | 29.531 | 1.00 | 22.66 C |
| ATOM | 1281 | O | ALA | 158 | 37.059 | 16.002 | 30.629 | 1.00 | 20.82 O |
| ATOM | 1282 | N | LYS | 159 | 37.567 | 16.212 | 28.446 | 1.00 | 22.65 N |
| ATOM | 1283 | CA | LYS | 159 | 37.599 | 17.663 | 28.482 | 1.00 | 23.96 C |
| ATOM | 1284 | CB | LYS | 159 | 38.104 | 18.194 | 27.136 | 1.00 | 28.43 C |
| ATOM | 1285 | CG | LYS | 159 | 39.526 | 17.712 | 26.845 | 1.00 | 33.70 C |
| ATOM | 1286 | CD | LYS | 159 | 40.002 | 17.957 | 25.421 | 1.00 | 36.49 C |
| ATOM | 1287 | CE | LYS | 159 | 41.387 | 17.324 | 25.234 | 1.00 | 36.49 C |
| ATOM | 1288 | NZ | LYS | 159 | 41.914 | 17.388 | 23.834 | 1.00 | 39.43 N |
| ATOM | 1289 | C | LYS | 159 | 36.220 | 18.209 | 28.822 | 1.00 | 23.61 C |
| ATOM | 1290 | O | LYS | 159 | 36.096 | 19.269 | 29.426 | 1.00 | 22.68 O |
| ATOM | 1291 | N | ARG | 160 | 35.179 | 17.478 | 28.441 | 1.00 | 22.77 N |
| ATOM | 1292 | CA | ARG | 160 | 33.828 | 17.914 | 28.751 | 1.00 | 23.39 C |
| ATOM | 1293 | CB | ARG | 160 | 32.819 | 17.201 | 27.844 | 1.00 | 24.29 C |
| ATOM | 1294 | CG | ARG | 160 | 32.937 | 17.636 | 26.383 | 1.00 | 28.21 C |
| ATOM | 1295 | CD | ARG | 160 | 31.916 | 16.937 | 25.508 | 1.00 | 30.52 C |
| ATOM | 1296 | NE | ARG | 160 | 30.559 | 17.165 | 25.986 | 1.00 | 32.81 N |
| ATOM | 1297 | CZ | ARG | 160 | 29.499 | 16.487 | 25.563 | 1.00 | 35.18 C |
| ATOM | 1298 | NH1 | ARG | 160 | 28.298 | 16.761 | 26.054 | 1.00 | 34.50 N |
| ATOM | 1299 | NH2 | ARG | 160 | 29.643 | 15.529 | 24.655 | 1.00 | 33.24 N |
| ATOM | 1300 | C | ARG | 160 | 33.526 | 17.657 | 30.227 | 1.00 | 22.94 C |
| ATOM | 1301 | O | ARG | 160 | 32.819 | 18.438 | 30.859 | 1.00 | 23.10 O |
| ATOM | 1302 | N | TYR | 161 | 34.055 | 16.570 | 30.787 | 1.00 | 22.17 N |
| ATOM | 1303 | CA | TYR | 161 | 33.826 | 16.304 | 32.207 | 1.00 | 22.32 C |
| ATOM | 1304 | CB | TYR | 161 | 34.322 | 14.921 | 32.617 | 1.00 | 22.26 C |
| ATOM | 1305 | CG | TYR | 161 | 33.319 | 13.812 | 32.437 | 1.00 | 22.40 C |
| ATOM | 1306 | CD1 | TYR | 161 | 33.208 | 13.137 | 31.224 | 1.00 | 23.51 C |
| ATOM | 1307 | CE1 | TYR | 161 | 32.324 | 12.062 | 31.077 | 1.00 | 23.70 C |
| ATOM | 1308 | CD2 | TYR | 161 | 32.512 | 13.396 | 33.500 | 1.00 | 21.24 C |
| ATOM | 1309 | CE2 | TYR | 161 | 31.629 | 12.327 | 33.358 | 1.00 | 23.56 C |
| ATOM | 1310 | CZ | TYR | 161 | 31.546 | 11.661 | 32.146 | 1.00 | 23.86 C |
| ATOM | 1311 | OH | TYR | 161 | 30.725 | 10.558 | 32.016 | 1.00 | 24.68 O |
| ATOM | 1312 | C | TYR | 161 | 34.584 | 17.337 | 33.017 | 1.00 | 22.45 C |
| ATOM | 1313 | O | TYR | 161 | 34.088 | 17.848 | 34.021 | 1.00 | 23.97 O |
| ATOM | 1314 | N | LYS | 162 | 35.800 | 17.633 | 32.581 | 1.00 | 22.47 N |
| ATOM | 1315 | CA | LYS | 162 | 36.622 | 18.609 | 33.269 | 1.00 | 23.35 C |
| ATOM | 1316 | CB | LYS | 162 | 37.949 | 18.796 | 32.537 | 1.00 | 25.48 C |
| ATOM | 1317 | CG | LYS | 162 | 38.951 | 19.677 | 33.275 | 1.00 | 29.28 C |
| ATOM | 1318 | CD | LYS | 162 | 40.323 | 19.592 | 32.619 | 1.00 | 32.83 C |
| ATOM | 1319 | CE | LYS | 162 | 41.373 | 20.335 | 33.424 | 1.00 | 34.63 C |
| ATOM | 1320 | NZ | LYS | 162 | 42.733 | 20.156 | 32.844 | 1.00 | 37.31 N |
| ATOM | 1321 | C | LYS | 162 | 35.867 | 19.929 | 33.351 | 1.00 | 24.15 C |
| ATOM | 1322 | O | LYS | 162 | 35.819 | 20.551 | 34.407 | 1.00 | 23.68 O |
| ATOM | 1323 | N | ALA | 163 | 35.255 | 20.340 | 32.243 | 1.00 | 23.61 N |
| ATOM | 1324 | CA | ALA | 163 | 34.496 | 21.586 | 32.217 | 1.00 | 24.66 C |
| ATOM | 1325 | CB | ALA | 163 | 34.029 | 21.888 | 30.793 | 1.00 | 25.16 C |
| ATOM | 1326 | C | ALA | 163 | 33.293 | 21.531 | 33.155 | 1.00 | 25.18 C |
| ATOM | 1327 | O | ALA | 163 | 32.994 | 22.506 | 33.851 | 1.00 | 23.19 O |
| ATOM | 1328 | N | ALA | 164 | 32.602 | 20.392 | 33.161 | 1.00 | 24.67 N |
| ATOM | 1329 | CA | ALA | 164 | 31.434 | 20.206 | 34.011 | 1.00 | 23.89 C |
| ATOM | 1330 | CB | ALA | 164 | 30.837 | 18.823 | 33.784 | 1.00 | 24.91 C |
| ATOM | 1331 | C | ALA | 164 | 31.805 | 20.378 | 35.480 | 1.00 | 24.76 C |
| ATOM | 1332 | O | ALA | 164 | 31.129 | 21.084 | 36.217 | 1.00 | 24.38 O |
| ATOM | 1333 | N | PHE | 165 | 32.879 | 19.723 | 35.901 | 1.00 | 23.75 N |
| ATOM | 1334 | CA | PHE | 165 | 33.330 | 19.816 | 37.284 | 1.00 | 25.72 C |
| ATOM | 1335 | CB | PHE | 165 | 34.400 | 18.760 | 37.550 | 1.00 | 24.54 C |
| ATOM | 1336 | CG | PHE | 165 | 33.837 | 17.403 | 37.824 | 1.00 | 26.46 C |
| ATOM | 1337 | CD1 | PHE | 165 | 33.280 | 17.110 | 39.064 | 1.00 | 27.51 C |
| ATOM | 1338 | CD2 | PHE | 165 | 33.829 | 16.426 | 36.839 | 1.00 | 24.70 C |
| ATOM | 1339 | CE1 | PHE | 165 | 32.722 | 15.859 | 39.318 | 1.00 | 27.32 C |
| ATOM | 1340 | CE2 | PHE | 165 | 33.272 | 15.172 | 37.084 | 1.00 | 25.28 C |
| ATOM | 1341 | CZ | PHE | 165 | 32.719 | 14.890 | 38.325 | 1.00 | 26.20 C |
| ATOM | 1342 | C | PHE | 165 | 33.868 | 21.194 | 37.639 | 1.00 | 27.02 C |

-continued

| | | | | | | | | |
|---|---|---|---|---|---|---|---|---|
| ATOM | 1343 | O | PHE | 165 | 33.647 | 21.690 | 38.747 | 1.00 | 26.95 | O |
| ATOM | 1344 | N | THR | 166 | 34.576 | 21.806 | 36.696 | 1.00 | 26.67 | N |
| ATOM | 1345 | CA | THR | 166 | 35.146 | 23.128 | 36.910 | 1.00 | 28.42 | C |
| ATOM | 1346 | CB | THR | 166 | 35.966 | 23.573 | 35.688 | 1.00 | 28.67 | C |
| ATOM | 1347 | OG1 | THR | 166 | 37.099 | 22.710 | 35.541 | 1.00 | 28.72 | O |
| ATOM | 1348 | CG2 | THR | 166 | 36.438 | 25.017 | 35.856 | 1.00 | 30.22 | C |
| ATOM | 1349 | C | THR | 166 | 34.057 | 24.159 | 37.173 | 1.00 | 27.78 | C |
| ATOM | 1350 | O | THR | 166 | 34.162 | 24.970 | 38.094 | 1.00 | 29.29 | O |
| ATOM | 1351 | N | GLU | 167 | 33.008 | 24.114 | 36.365 | 1.00 | 28.67 | N |
| ATOM | 1352 | CA | GLU | 167 | 31.905 | 25.048 | 36.498 | 1.00 | 29.33 | C |
| ATOM | 1353 | CB | GLU | 167 | 31.068 | 25.070 | 35.219 | 1.00 | 30.56 | C |
| ATOM | 1354 | CG | GLU | 167 | 29.766 | 25.841 | 35.382 | 1.00 | 32.73 | C |
| ATOM | 1355 | CD | GLU | 167 | 28.817 | 25.673 | 34.218 | 1.00 | 33.21 | C |
| ATOM | 1356 | OE1 | GLU | 167 | 27.734 | 26.295 | 34.245 | 1.00 | 36.42 | O |
| ATOM | 1357 | OE2 | GLU | 167 | 29.146 | 24.924 | 33.278 | 1.00 | 32.03 | O |
| ATOM | 1358 | C | GLU | 167 | 30.975 | 24.731 | 37.657 | 1.00 | 30.62 | C |
| ATOM | 1359 | O | GLU | 167 | 30.626 | 25.602 | 38.458 | 1.00 | 28.60 | O |
| ATOM | 1360 | N | CYS | 168 | 30.568 | 23.473 | 37.735 | 1.00 | 27.70 | N |
| ATOM | 1361 | CA | CYS | 168 | 29.630 | 23.054 | 38.752 | 1.00 | 29.04 | C |
| ATOM | 1362 | C | CYS | 168 | 30.121 | 22.921 | 40.179 | 1.00 | 28.27 | C |
| ATOM | 1363 | O | CYS | 168 | 29.335 | 23.061 | 41.114 | 1.00 | 29.41 | O |
| ATOM | 1364 | CB | CYS | 168 | 28.977 | 21.752 | 38.318 | 1.00 | 28.12 | C |
| ATOM | 1365 | SG | CYS | 168 | 27.921 | 21.910 | 36.848 | 1.00 | 27.31 | S |
| ATOM | 1366 | N | CYS | 169 | 31.405 | 22.662 | 40.374 | 1.00 | 27.98 | N |
| ATOM | 1367 | CA | CYS | 169 | 31.888 | 22.507 | 41.734 | 1.00 | 29.91 | C |
| ATOM | 1368 | C | CYS | 169 | 32.060 | 23.801 | 42.516 | 1.00 | 32.10 | C |
| ATOM | 1369 | O | CYS | 169 | 32.329 | 23.769 | 43.713 | 1.00 | 32.90 | O |
| ATOM | 1370 | CB | CYS | 169 | 33.185 | 21.717 | 41.742 | 1.00 | 28.75 | C |
| ATOM | 1371 | SG | CYS | 169 | 32.940 | 19.960 | 41.320 | 1.00 | 27.95 | S |
| ATOM | 1372 | N | GLN | 170 | 31.914 | 24.937 | 41.844 | 1.00 | 34.07 | N |
| ATOM | 1373 | CA | GLN | 170 | 32.039 | 26.225 | 42.516 | 1.00 | 36.89 | C |
| ATOM | 1374 | CB | GLN | 170 | 33.235 | 27.013 | 41.967 | 1.00 | 39.05 | C |
| ATOM | 1375 | CG | GLN | 170 | 33.359 | 27.028 | 40.453 | 1.00 | 43.03 | C |
| ATOM | 1376 | CD | GLN | 170 | 34.626 | 27.730 | 39.987 | 1.00 | 44.37 | C |
| ATOM | 1377 | OE1 | GLN | 170 | 34.748 | 28.952 | 40.094 | 1.00 | 45.73 | O |
| ATOM | 1378 | NE2 | GLN | 170 | 35.580 | 26.957 | 39.478 | 1.00 | 44.70 | N |
| ATOM | 1379 | C | GLN | 170 | 30.753 | 27.018 | 42.348 | 1.00 | 36.48 | C |
| ATOM | 1380 | O | GLN | 170 | 30.720 | 28.232 | 42.546 | 1.00 | 36.94 | O |
| ATOM | 1381 | N | ALA | 171 | 29.689 | 26.313 | 41.986 | 1.00 | 35.53 | N |
| ATOM | 1382 | CA | ALA | 171 | 28.391 | 26.940 | 41.799 | 1.00 | 36.43 | C |
| ATOM | 1383 | CB | ALA | 171 | 27.594 | 26.183 | 40.746 | 1.00 | 34.62 | C |
| ATOM | 1384 | C | ALA | 171 | 27.636 | 26.947 | 43.125 | 1.00 | 36.32 | C |
| ATOM | 1385 | O | ALA | 171 | 28.048 | 26.294 | 44.085 | 1.00 | 35.91 | O |
| ATOM | 1386 | N | ALA | 172 | 26.536 | 27.691 | 43.171 | 1.00 | 36.11 | N |
| ATOM | 1387 | CA | ALA | 172 | 25.718 | 27.769 | 44.374 | 1.00 | 37.38 | C |
| ATOM | 1388 | CB | ALA | 172 | 24.667 | 28.860 | 44.225 | 1.00 | 37.30 | C |
| ATOM | 1389 | C | ALA | 172 | 25.047 | 26.423 | 44.604 | 1.00 | 36.99 | C |
| ATOM | 1390 | O | ALA | 172 | 25.080 | 25.880 | 45.709 | 1.00 | 37.10 | O |
| ATOM | 1391 | N | ASP | 173 | 24.435 | 25.885 | 43.555 | 1.00 | 36.21 | N |
| ATOM | 1392 | CA | ASP | 173 | 23.774 | 24.594 | 43.657 | 1.00 | 35.77 | C |
| ATOM | 1393 | CB | ASP | 173 | 22.340 | 24.683 | 43.144 | 1.00 | 36.43 | C |
| ATOM | 1394 | CG | ASP | 173 | 21.530 | 23.448 | 43.476 | 1.00 | 39.19 | C |
| ATOM | 1395 | OD1 | ASP | 173 | 20.301 | 23.463 | 43.251 | 1.00 | 41.76 | O |
| ATOM | 1396 | OD2 | ASP | 173 | 22.123 | 22.456 | 43.958 | 1.00 | 39.06 | O |
| ATOM | 1397 | C | ASP | 173 | 24.564 | 23.582 | 42.840 | 1.00 | 34.19 | C |
| ATOM | 1398 | O | ASP | 173 | 24.194 | 23.244 | 41.722 | 1.00 | 34.19 | O |
| ATOM | 1399 | N | LYS | 174 | 25.660 | 23.111 | 43.422 | 1.00 | 33.55 | N |
| ATOM | 1400 | CA | LYS | 174 | 26.547 | 22.153 | 42.778 | 1.00 | 32.09 | C |
| ATOM | 1401 | CB | LYS | 174 | 27.558 | 21.622 | 43.800 | 1.00 | 31.57 | C |
| ATOM | 1402 | CG | LYS | 174 | 28.439 | 22.719 | 44.383 | 1.00 | 33.11 | C |
| ATOM | 1403 | CD | LYS | 174 | 29.484 | 22.192 | 45.355 | 1.00 | 34.10 | C |
| ATOM | 1404 | CE | LYS | 174 | 30.330 | 23.339 | 45.913 | 1.00 | 34.70 | C |
| ATOM | 1405 | NZ | LYS | 174 | 31.438 | 22.862 | 46.785 | 1.00 | 32.16 | N |
| ATOM | 1406 | C | LYS | 174 | 25.833 | 20.997 | 42.084 | 1.00 | 31.19 | C |
| ATOM | 1407 | O | LYS | 174 | 26.006 | 20.797 | 40.884 | 1.00 | 29.30 | O |
| ATOM | 1408 | N | ALA | 175 | 25.019 | 20.253 | 42.827 | 1.00 | 29.90 | N |
| ATOM | 1409 | CA | ALA | 175 | 24.310 | 19.115 | 42.257 | 1.00 | 30.27 | C |
| ATOM | 1410 | CB | ALA | 175 | 23.528 | 18.379 | 43.348 | 1.00 | 31.51 | C |
| ATOM | 1411 | C | ALA | 175 | 23.379 | 19.472 | 41.104 | 1.00 | 31.06 | C |
| ATOM | 1412 | O | ALA | 175 | 23.363 | 18.787 | 40.079 | 1.00 | 30.11 | O |
| ATOM | 1413 | N | ALA | 176 | 22.599 | 20.537 | 41.268 | 1.00 | 30.08 | N |
| ATOM | 1414 | CA | ALA | 176 | 21.661 | 20.954 | 40.229 | 1.00 | 31.61 | C |
| ATOM | 1415 | CB | ALA | 176 | 20.908 | 22.200 | 40.678 | 1.00 | 32.83 | C |
| ATOM | 1416 | C | ALA | 176 | 22.375 | 21.229 | 38.911 | 1.00 | 30.95 | C |
| ATOM | 1417 | O | ALA | 176 | 21.825 | 21.022 | 37.832 | 1.00 | 31.05 | O |
| ATOM | 1418 | N | CYS | 177 | 23.607 | 21.697 | 39.022 | 1.00 | 31.02 | N |
| ATOM | 1419 | CA | CYS | 177 | 24.441 | 22.027 | 37.875 | 1.00 | 31.16 | C |
| ATOM | 1420 | C | CYS | 177 | 25.154 | 20.794 | 37.330 | 1.00 | 29.17 | C |
| ATOM | 1421 | O | CYS | 177 | 25.102 | 20.504 | 36.135 | 1.00 | 26.73 | O |

-continued

| | | | | | | | | | |
|---|---|---|---|---|---|---|---|---|---|
| ATOM | 1422 | CB | CYS | 177 | 25.473 | 23.063 | 38.327 | 1.00 | 31.83 C |
| ATOM | 1423 | SG | CYS | 177 | 26.816 | 23.583 | 37.205 | 1.00 | 34.69 S |
| ATOM | 1424 | N | LEU | 178 | 25.811 | 20.075 | 38.234 | 1.00 | 27.72 N |
| ATOM | 1425 | CA | LEU | 178 | 26.602 | 18.896 | 37.896 | 1.00 | 26.57 C |
| ATOM | 1426 | CB | LEU | 178 | 27.447 | 18.489 | 39.108 | 1.00 | 25.91 C |
| ATOM | 1427 | CG | LEU | 178 | 28.925 | 18.144 | 38.896 | 1.00 | 28.89 C |
| ATOM | 1428 | CD1 | LEU | 178 | 29.349 | 17.175 | 39.988 | 1.00 | 25.58 C |
| ATOM | 1429 | CD2 | LEU | 178 | 29.167 | 17.538 | 37.523 | 1.00 | 26.61 C |
| ATOM | 1430 | C | LEU | 178 | 25.881 | 17.651 | 37.380 | 1.00 | 24.80 C |
| ATOM | 1431 | O | LEU | 178 | 26.206 | 17.149 | 36.303 | 1.00 | 25.41 O |
| ATOM | 1432 | N | LEU | 179 | 24.924 | 17.144 | 38.149 | 1.00 | 22.68 N |
| ATOM | 1433 | CA | LEU | 179 | 24.217 | 15.922 | 37.775 | 1.00 | 24.35 C |
| ATOM | 1434 | CB | LEU | 179 | 23.125 | 15.594 | 38.803 | 1.00 | 24.85 C |
| ATOM | 1435 | CG | LEU | 179 | 23.638 | 15.145 | 40.176 | 1.00 | 25.93 C |
| ATOM | 1436 | CD1 | LEU | 179 | 24.669 | 14.039 | 40.026 | 1.00 | 27.87 C |
| ATOM | 1437 | CD2 | LEU | 179 | 24.264 | 16.300 | 40.878 | 1.00 | 31.20 C |
| ATOM | 1438 | C | LEU | 179 | 23.644 | 15.872 | 36.366 | 1.00 | 24.16 C |
| ATOM | 1439 | O | LEU | 179 | 23.842 | 14.891 | 35.656 | 1.00 | 23.34 O |
| ATOM | 1440 | N | PRO | 180 | 22.918 | 16.915 | 35.940 | 1.00 | 24.79 N |
| ATOM | 1441 | CD | PRO | 180 | 22.363 | 18.077 | 36.660 | 1.00 | 26.35 C |
| ATOM | 1442 | CA | PRO | 180 | 22.387 | 16.841 | 34.578 | 1.00 | 25.66 C |
| ATOM | 1443 | CB | PRO | 180 | 21.637 | 18.163 | 34.431 | 1.00 | 27.05 C |
| ATOM | 1444 | CG | PRO | 180 | 21.135 | 18.410 | 35.826 | 1.00 | 27.13 C |
| ATOM | 1445 | C | PRO | 180 | 23.514 | 16.692 | 33.554 | 1.00 | 24.94 C |
| ATOM | 1446 | O | PRO | 180 | 23.363 | 16.016 | 32.543 | 1.00 | 23.29 O |
| ATOM | 1447 | N | LYS | 181 | 24.648 | 17.330 | 33.821 | 1.00 | 25.66 N |
| ATOM | 1448 | CA | LYS | 181 | 25.775 | 17.248 | 32.904 | 1.00 | 26.06 C |
| ATOM | 1449 | CB | LYS | 181 | 26.833 | 18.294 | 33.268 | 1.00 | 26.88 C |
| ATOM | 1450 | CG | LYS | 181 | 26.350 | 19.730 | 33.099 | 1.00 | 29.31 C |
| ATOM | 1451 | CD | LYS | 181 | 27.406 | 20.737 | 33.521 | 1.00 | 30.97 C |
| ATOM | 1452 | CE | LYS | 181 | 26.900 | 22.166 | 33.354 | 1.00 | 31.56 C |
| ATOM | 1453 | NZ | LYS | 181 | 26.605 | 22.490 | 31.930 | 1.00 | 34.87 N |
| ATOM | 1454 | C | LYS | 181 | 26.378 | 15.845 | 32.919 | 1.00 | 24.07 C |
| ATOM | 1455 | O | LYS | 181 | 26.760 | 15.318 | 31.877 | 1.00 | 23.35 O |
| ATOM | 1456 | N | LEU | 182 | 26.459 | 15.243 | 34.101 | 1.00 | 24.47 N |
| ATOM | 1457 | CA | LEU | 182 | 27.006 | 13.896 | 34.225 | 1.00 | 25.75 C |
| ATOM | 1458 | CB | LEU | 182 | 27.220 | 13.532 | 35.698 | 1.00 | 24.72 C |
| ATOM | 1459 | CG | LEU | 182 | 28.266 | 14.366 | 36.448 | 1.00 | 24.56 C |
| ATOM | 1460 | CD1 | LEU | 182 | 28.369 | 13.893 | 37.886 | 1.00 | 24.18 C |
| ATOM | 1461 | CD2 | LEU | 182 | 29.613 | 14.242 | 35.755 | 1.00 | 23.06 C |
| ATOM | 1462 | C | LEU | 182 | 26.053 | 12.903 | 33.565 | 1.00 | 26.04 C |
| ATOM | 1463 | O | LEU | 182 | 26.487 | 11.927 | 32.949 | 1.00 | 25.29 O |
| ATOM | 1464 | N | ASP | 183 | 24.755 | 13.158 | 33.698 | 1.56 | 27.42 N |
| ATOM | 1465 | CA | ASP | 183 | 23.751 | 12.302 | 33.082 | 1.00 | 28.92 C |
| ATOM | 1466 | CB | ASP | 183 | 22.337 | 12.784 | 33.424 | 1.00 | 30.09 C |
| ATOM | 1467 | CG | ASP | 183 | 21.888 | 12.378 | 34.819 | 1.00 | 32.33 C |
| ATOM | 1468 | OD1 | ASP | 183 | 20.739 | 12.716 | 35.181 | 1.00 | 33.14 O |
| ATOM | 1469 | OD2 | ASP | 183 | 22.666 | 11.727 | 35.552 | 1.00 | 32.75 O |
| ATOM | 1470 | C | ASP | 183 | 23.941 | 12.350 | 31.566 | 1.00 | 28.35 C |
| ATOM | 1471 | O | ASP | 183 | 23.942 | 11.313 | 30.904 | 1.00 | 29.41 O |
| ATOM | 1472 | N | GLU | 184 | 24.095 | 13.557 | 31.023 | 1.00 | 28.13 N |
| ATOM | 1473 | CA | GLU | 184 | 24.287 | 13.730 | 29.584 | 1.00 | 29.50 C |
| ATOM | 1474 | CB | GLU | 184 | 24.382 | 15.213 | 29.216 | 1.00 | 32.17 C |
| ATOM | 1475 | CG | GLU | 184 | 23.108 | 16.013 | 29.433 | 1.00 | 38.93 C |
| ATOM | 1476 | CD | GLU | 184 | 23.186 | 17.414 | 28.830 | 1.00 | 43.43 C |
| ATOM | 1477 | OE1 | GLU | 184 | 22.236 | 18.208 | 29.029 | 1.00 | 45.37 O |
| ATOM | 1478 | OE2 | GLU | 184 | 24.195 | 17.721 | 28.153 | 1.00 | 44.53 O |
| ATOM | 1479 | C | GLU | 184 | 25.546 | 13.013 | 29.095 | 1.00 | 27.76 C |
| ATOM | 1480 | O | GLU | 184 | 25.486 | 12.215 | 28.162 | 1.00 | 28.37 O |
| ATOM | 1481 | N | LEU | 185 | 26.682 | 13.299 | 29.726 | 1.00 | 26.01 N |
| ATOM | 1482 | CA | LEU | 185 | 27.946 | 12.665 | 29.351 | 1.00 | 24.13 C |
| ATOM | 1483 | CB | LEU | 185 | 29.068 | 13.097 | 30.301 | 1.00 | 23.78 C |
| ATOM | 1484 | CG | LEU | 185 | 29.920 | 14.337 | 30.011 | 1.00 | 26.40 C |
| ATOM | 1485 | CD1 | LEU | 185 | 29.773 | 14.749 | 28.557 | 1.00 | 23.77 C |
| ATOM | 1486 | CD2 | LEU | 185 | 29.531 | 15.458 | 30.947 | 1.00 | 24.62 C |
| ATOM | 1487 | C | LEU | 185 | 27.835 | 11.145 | 29.388 | 1.00 | 23.55 C |
| ATOM | 1488 | O | LEU | 185 | 28.290 | 10.447 | 28.482 | 1.00 | 24.27 O |
| ATOM | 1489 | N | ARG | 186 | 27.246 | 10.637 | 30.461 | 1.00 | 23.87 N |
| ATOM | 1490 | CA | ARG | 186 | 27.062 | 9.205 | 30.634 | 1.00 | 25.88 C |
| ATOM | 1491 | CB | ARG | 186 | 26.352 | 8.959 | 31.969 | 1.00 | 29.61 C |
| ATOM | 1492 | CG | ARG | 186 | 26.140 | 7.514 | 32.363 | 1.00 | 33.22 C |
| ATOM | 1493 | CD | ARG | 186 | 24.849 | 6.945 | 31.803 | 1.00 | 37.79 C |
| ATOM | 1494 | NE | ARG | 186 | 23.697 | 7.810 | 32.055 | 1.00 | 41.24 N |
| ATOM | 1495 | CZ | ARG | 186 | 23.229 | 8.134 | 33.258 | 1.00 | 40.76 C |
| ATOM | 1496 | NH1 | ARG | 186 | 22.174 | 8.929 | 33.361 | 1.00 | 41.85 N |
| ATOM | 1497 | NH2 | ARG | 186 | 23.805 | 7.669 | 34.356 | 1.00 | 42.94 N |
| ATOM | 1498 | C | ARG | 186 | 26.254 | 8.628 | 29.471 | 1.00 | 26.22 C |
| ATOM | 1499 | O | ARG | 186 | 26.642 | 7.617 | 28.868 | 1.00 | 24.27 O |
| ATOM | 1500 | N | ASP | 187 | 25.137 | 9.276 | 29.153 | 1.00 | 25.62 N |

-continued

| ATOM | 1501 | CA  | ASP | 187 | 24.283 | 8.813  | 28.067 | 1.00 | 28.35 | C |
| ---- | ---- | --- | --- | --- | ------ | ------ | ------ | ---- | ----- | - |
| ATOM | 1502 | CB  | ASP | 187 | 22.992 | 9.645  | 27.985 | 1.00 | 29.91 | C |
| ATOM | 1503 | CG  | ASP | 187 | 22.127 | 9.517  | 29.233 | 1.00 | 33.76 | C |
| ATOM | 1504 | OD1 | ASP | 187 | 22.072 | 8.414  | 29.818 | 1.00 | 33.68 | O |
| ATOM | 1505 | OD2 | ASP | 187 | 21.489 | 10.521 | 29.622 | 1.00 | 36.36 | O |
| ATOM | 1506 | C   | ASP | 187 | 25.013 | 8.872  | 26.731 | 1.00 | 26.67 | C |
| ATOM | 1507 | O   | ASP | 187 | 24.990 | 7.912  | 25.968 | 1.00 | 25.93 | O |
| ATOM | 1508 | N   | GLU | 188 | 25.652 | 10.000 | 26.443 | 1.00 | 27.13 | N |
| ATOM | 1509 | CA  | GLU | 188 | 26.379 | 10.138 | 25.185 | 1.00 | 28.40 | C |
| ATOM | 1510 | CB  | GLU | 188 | 27.022 | 11.520 | 25.075 | 1.00 | 30.92 | C |
| ATOM | 1511 | CG  | GLU | 188 | 26.047 | 12.648 | 24.849 | 1.00 | 34.96 | C |
| ATOM | 1512 | CD  | GLU | 188 | 26.747 | 13.977 | 24.655 | 1.00 | 36.94 | C |
| ATOM | 1513 | OE1 | GLU | 188 | 27.564 | 14.091 | 23.714 | 1.00 | 39.19 | O |
| ATOM | 1514 | OE2 | GLU | 188 | 26.479 | 14.906 | 25.443 | 1.00 | 39.17 | O |
| ATOM | 1515 | C   | GLU | 188 | 27.461 | 9.073  | 25.090 | 1.00 | 26.53 | C |
| ATOM | 1516 | O   | GLU | 188 | 27.699 | 8.506  | 24.023 | 1.00 | 25.50 | O |
| ATOM | 1517 | N   | GLY | 189 | 28.122 | 8.819  | 26.213 | 1.00 | 26.17 | N |
| ATOM | 1518 | CA  | GLY | 189 | 29.166 | 7.815  | 26.242 | 1.00 | 25.87 | C |
| ATOM | 1519 | C   | GLY | 189 | 28.638 | 6.440  | 25.881 | 1.00 | 26.92 | C |
| ATOM | 1520 | O   | GLY | 189 | 29.176 | 5.767  | 25.000 | 1.00 | 26.55 | O |
| ATOM | 1521 | N   | LYS | 190 | 27.584 | 6.010  | 26.564 | 1.00 | 26.90 | N |
| ATOM | 1522 | CA  | LYS | 190 | 27.007 | 4.698  | 26.289 | 1.00 | 26.46 | C |
| ATOM | 1523 | CB  | LYS | 190 | 25.833 | 4.430  | 27.232 | 1.00 | 27.78 | C |
| ATOM | 1524 | CG  | LYS | 190 | 26.173 | 4.667  | 28.695 | 1.00 | 31.57 | C |
| ATOM | 1525 | CD  | LYS | 190 | 25.014 | 4.309  | 29.605 | 1.00 | 34.60 | C |
| ATOM | 1526 | CE  | LYS | 190 | 25.091 | 2.853  | 30.022 | 1.00 | 36.99 | C |
| ATOM | 1527 | NZ  | LYS | 190 | 26.221 | 2.633  | 30.971 | 1.00 | 37.56 | N |
| ATOM | 1528 | C   | LYS | 190 | 26.547 | 4.632  | 24.839 | 1.00 | 25.07 | C |
| ATOM | 1529 | O   | LYS | 190 | 26.793 | 3.645  | 24.148 | 1.00 | 25.14 | O |
| ATOM | 1530 | N   | ALA | 191 | 25.893 | 5.694  | 24.379 | 1.00 | 23.99 | N |
| ATOM | 1531 | CA  | ALA | 191 | 25.409 | 5.751  | 23.005 | 1.00 | 24.91 | C |
| ATOM | 1532 | CB  | ALA | 191 | 24.663 | 7.063  | 22.760 | 1.00 | 24.71 | C |
| ATOM | 1533 | C   | ALA | 191 | 26.564 | 5.617  | 22.019 | 1.00 | 24.18 | C |
| ATOM | 1534 | O   | ALA | 191 | 26.514 | 4.798  | 21.104 | 1.00 | 25.26 | O |
| ATOM | 1535 | N   | SER | 192 | 27.602 | 6.428  | 22.198 | 1.00 | 24.28 | N |
| ATOM | 1536 | CA  | SER | 192 | 28.755 | 6.372  | 21.309 | 1.00 | 22.65 | C |
| ATOM | 1537 | CB  | SER | 192 | 29.838 | 7.345  | 21.777 | 1.00 | 24.88 | C |
| ATOM | 1538 | OG  | SER | 192 | 31.042 | 7.122  | 21.072 | 1.00 | 27.17 | O |
| ATOM | 1539 | C   | SER | 192 | 29.321 | 4.957  | 21.253 | 1.00 | 23.24 | C |
| ATOM | 1540 | O   | SER | 192 | 29.632 | 4.446  | 20.179 | 1.00 | 21.91 | O |
| ATOM | 1541 | N   | SER | 193 | 29.446 | 4.319  | 22.411 | 1.00 | 24.41 | N |
| ATOM | 1542 | CA  | SER | 193 | 29.975 | 2.961  | 22.459 | 1.00 | 26.29 | C |
| ATOM | 1543 | CB  | SER | 193 | 30.124 | 2.509  | 23.911 | 1.00 | 26.81 | C |
| ATOM | 1544 | OG  | SER | 193 | 30.633 | 1.189  | 23.975 | 1.00 | 32.97 | O |
| ATOM | 1545 | C   | SER | 193 | 29.050 | 2.000  | 21.702 | 1.00 | 27.89 | C |
| ATOM | 1546 | O   | SER | 193 | 29.511 | 1.156  | 20.926 | 1.00 | 27.93 | O |
| ATOM | 1547 | N   | ALA | 194 | 27.747 | 2.137  | 21.930 | 1.00 | 26.46 | N |
| ATOM | 1548 | CA  | ALA | 194 | 26.754 | 1.291  | 21.268 | 1.00 | 28.27 | C |
| ATOM | 1549 | CB  | ALA | 194 | 25.355 | 1.606  | 21.808 | 1.00 | 25.08 | C |
| ATOM | 1550 | C   | ALA | 194 | 26.796 | 1.536  | 19.759 | 1.00 | 27.33 | C |
| ATOM | 1551 | O   | ALA | 194 | 26.775 | 0.599  | 18.963 | 1.00 | 28.34 | O |
| ATOM | 1552 | N   | LYS | 195 | 26.849 | 2.808  | 19.387 | 1.00 | 27.59 | N |
| ATOM | 1553 | CA  | LYS | 195 | 26.894 | 3.218  | 17.991 | 1.00 | 29.17 | C |
| ATOM | 1554 | CB  | LYS | 195 | 26.910 | 4.741  | 17.909 | 1.00 | 30.90 | C |
| ATOM | 1555 | CG  | LYS | 195 | 26.945 | 5.293  | 16.500 | 1.00 | 33.88 | C |
| ATOM | 1556 | CD  | LYS | 195 | 26.958 | 6.816  | 16.515 | 1.00 | 38.36 | C |
| ATOM | 1557 | CE  | LYS | 195 | 25.715 | 7.375  | 17.199 | 1.00 | 39.12 | C |
| ATOM | 1558 | NZ  | LYS | 195 | 25.656 | 8.863  | 17.127 | 1.00 | 41.92 | N |
| ATOM | 1559 | C   | LYS | 195 | 28.124 | 2.653  | 17.296 | 1.00 | 29.62 | C |
| ATOM | 1560 | O   | LYS | 195 | 28.045 | 2.165  | 16.162 | 1.00 | 28.45 | O |
| ATOM | 1561 | N   | GLN | 196 | 29.263 | 2.725  | 17.977 | 1.00 | 28.61 | N |
| ATOM | 1562 | CA  | GLN | 196 | 30.511 | 2.209  | 17.423 | 1.00 | 29.56 | C |
| ATOM | 1563 | CB  | GLN | 196 | 31.680 | 2.458  | 18.398 | 1.00 | 28.99 | C |
| ATOM | 1564 | CG  | GLN | 196 | 32.103 | 3.930  | 18.525 | 1.00 | 31.76 | C |
| ATOM | 1565 | CD  | GLN | 196 | 33.213 | 4.169  | 19.560 | 1.00 | 33.58 | C |
| ATOM | 1566 | OE1 | GLN | 196 | 34.333 | 3.667  | 19.427 | 1.00 | 31.96 | O |
| ATOM | 1567 | NE2 | GLN | 196 | 32.898 | 4.944  | 20.592 | 1.00 | 31.16 | N |
| ATOM | 1568 | C   | GLN | 196 | 30.368 | 0.714  | 17.137 | 1.00 | 29.06 | C |
| ATOM | 1569 | O   | GLN | 196 | 30.825 | 0.227  | 16.107 | 1.00 | 27.73 | O |
| ATOM | 1570 | N   | ARG | 197 | 29.714 | −0.011 | 18.039 | 1.00 | 30.08 | N |
| ATOM | 1571 | CA  | ARG | 197 | 29.542 | −1.451 | 17.850 | 1.00 | 32.15 | C |
| ATOM | 1572 | CB  | ARG | 197 | 29.176 | −2.128 | 19.175 | 1.00 | 34.50 | C |
| ATOM | 1573 | CG  | ARG | 197 | 29.819 | −3.503 | 19.340 | 1.00 | 40.58 | C |
| ATOM | 1574 | CD  | ARG | 197 | 28.795 | −4.610 | 19.549 | 1.00 | 43.25 | C |
| ATOM | 1575 | NE  | ARG | 197 | 28.059 | −4.461 | 20.804 | 1.00 | 46.41 | N |
| ATOM | 1576 | CZ  | ARG | 197 | 27.225 | −5.373 | 21.297 | 1.00 | 47.58 | C |
| ATOM | 1577 | NH1 | ARG | 197 | 26.600 | −5.151 | 22.446 | 1.00 | 47.39 | N |
| ATOM | 1578 | NH2 | ARG | 197 | 27.019 | −6.513 | 20.645 | 1.00 | 48.93 | N |
| ATOM | 1579 | C   | ARG | 197 | 28.486 | −1.781 | 16.794 | 1.00 | 31.32 | C |

-continued

| | | | | | | | | | |
|---|---|---|---|---|---|---|---|---|---|
| ATOM | 1580 | O | ARG | 197 | 28.658 | −2.714 | 16.007 | 1.00 | 32.58 O |
| ATOM | 5145 | FE | HEM | 605 | 32.347 | 8.521 | 32.831 | 1.00 | 25.18 FE |
| ATOM | 5146 | CHA | HEM | 605 | 29.989 | 6.250 | 31.888 | 1.00 | 26.35 C |
| ATOM | 5147 | CHB | HEM | 605 | 33.685 | 8.455 | 29.666 | 1.00 | 23.94 C |
| ATOM | 5148 | CHC | HEM | 605 | 34.763 | 10.734 | 33.777 | 1.00 | 25.27 C |
| ATOM | 5149 | CHD | HEM | 605 | 31.090 | 8.531 | 35.950 | 1.00 | 25.17 C |
| ATOM | 5150 | NA | HEM | 605 | 31.911 | 7.566 | 31.106 | 1.00 | 24.86 N |
| ATOM | 5151 | C1A | HEM | 605 | 30.872 | 6.651 | 30.902 | 1.00 | 25.80 C |
| ATOM | 5152 | C2A | HEM | 605 | 30.847 | 6.163 | 29.510 | 1.00 | 27.42 C |
| ATOM | 5153 | C3A | HEM | 605 | 31.993 | 6.866 | 28.870 | 1.00 | 25.02 C |
| ATOM | 5154 | C4A | HEM | 605 | 32.588 | 7.675 | 29.870 | 1.00 | 24.52 C |
| ATOM | 5155 | CMA | HEM | 605 | 32.465 | 6.750 | 27.426 | 1.00 | 24.96 C |
| ATOM | 5156 | CAA | HEM | 605 | 29.882 | 5.186 | 28.930 | 1.00 | 29.17 C |
| ATOM | 5157 | CBA | HEM | 605 | 30.527 | 3.832 | 28.695 | 1.00 | 31.67 C |
| ATOM | 5158 | CGA | HEM | 605 | 29.518 | 2.774 | 28.376 | 1.00 | 33.06 C |
| ATOM | 5159 | O1A | HEM | 605 | 29.021 | 2.075 | 29.271 | 1.00 | 33.53 O |
| ATOM | 5160 | O2A | HEM | 605 | 29.206 | 2.620 | 27.150 | 1.00 | 37.12 O |
| ATOM | 5161 | NB | HEM | 605 | 33.905 | 9.412 | 31.936 | 1.00 | 24.76 N |
| ATOM | 5162 | C1B | HEM | 605 | 34.306 | 9.254 | 30.609 | 1.00 | 24.01 C |
| ATOM | 5163 | C2B | HEM | 605 | 35.509 | 10.069 | 30.357 | 1.00 | 25.66 C |
| ATOM | 5164 | C3B | HEM | 605 | 35.803 | 10.700 | 31.496 | 1.00 | 26.84 C |
| ATOM | 5165 | C4B | HEM | 605 | 34.802 | 10.285 | 32.456 | 1.00 | 24.41 C |
| ATOM | 5166 | CMB | HEM | 605 | 36.214 | 10.115 | 29.023 | 1.00 | 25.60 C |
| ATOM | 5167 | CAB | HEM | 605 | 36.940 | 11.662 | 31.787 | 1.00 | 28.37 C |
| ATOM | 5168 | CBB | HEM | 605 | 38.095 | 11.278 | 32.280 | 1.00 | 31.00 C |
| ATOM | 5169 | NC | HEM | 605 | 32.819 | 9.474 | 34.544 | 1.00 | 24.53 N |
| ATOM | 5170 | C1C | HEM | 605 | 33.853 | 10.372 | 34.756 | 1.00 | 25.60 C |
| ATOM | 5171 | C2C | HEM | 605 | 33.849 | 10.865 | 36.114 | 1.00 | 26.07 C |
| ATOM | 5172 | C3C | HEM | 605 | 32.809 | 10.235 | 36.722 | 1.00 | 26.20 C |
| ATOM | 5173 | C4C | HEM | 605 | 32.185 | 9.367 | 35.727 | 1.00 | 25.78 C |
| ATOM | 5174 | CMC | HEM | 605 | 34.846 | 11.872 | 36.654 | 1.00 | 26.02 C |
| ATOM | 5175 | CAC | HEM | 605 | 32.277 | 10.303 | 38.134 | 1.00 | 28.75 C |
| ATOM | 5176 | CBC | HEM | 605 | 32.723 | 11.023 | 39.147 | 1.00 | 29.46 C |
| ATOM | 5177 | ND | HEM | 605 | 30.822 | 7.568 | 33.762 | 1.00 | 24.98 N |
| ATOM | 5178 | C1D | HEM | 605 | 30.449 | 7.690 | 35.064 | 1.00 | 26.97 C |
| ATOM | 5179 | C2D | HEM | 605 | 29.334 | 6.838 | 35.372 | 1.00 | 27.95 C |
| ATOM | 5180 | C3D | HEM | 605 | 29.022 | 6.186 | 34.199 | 1.00 | 28.91 C |
| ATOM | 5181 | C4D | HEM | 605 | 29.960 | 6.655 | 33.195 | 1.00 | 26.41 C |
| ATOM | 5182 | CMD | HEM | 605 | 28.658 | 6.696 | 36.726 | 1.00 | 29.28 C |
| ATOM | 5183 | CAD | HEM | 605 | 27.918 | 5.166 | 34.005 | 1.00 | 30.52 C |
| ATOM | 5184 | CBD | HEM | 605 | 28.517 | 3.738 | 34.229 | 1.00 | 33.73 C |
| ATOM | 5185 | CGD | HEM | 605 | 27.558 | 2.594 | 34.062 | 1.00 | 36.10 C |
| ATOM | 5186 | O1D | HEM | 605 | 27.962 | 1.415 | 34.024 | 1.00 | 36.59 O |
| ATOM | 5187 | O2D | HEM | 605 | 26.323 | 2.857 | 33.954 | 1.00 | 38.61 O |
| ATOM | 4670 | OH2 | WAT | 1040 | 35.718 | 9.520 | 42.672 | 1.00 | 42.18 O |
| ATOM | 4688 | OH2 | WAT | 1058 | 28.964 | 10.656 | 33.920 | 1.00 | 22.72 O |
| ATOM | 4689 | OH2 | WAT | 1059 | 30.899 | 0.748 | 34.525 | 1.00 | 20.23 O |
| ATOM | 4729 | OH2 | WAT | 1099 | 27.275 | 9.551 | 36.040 | 1.00 | 39.65 O |
| ATOM | 4758 | OH2 | WAT | 1128 | 26.373 | 3.276 | 37.398 | 1.00 | 47.19 O |
| ATOM | 4782 | OH2 | WAT | 1152 | 25.763 | 5.450 | 39.695 | 1.00 | 46.21 O |
| ATOM | 4874 | OH2 | WAT | 1244 | 25.312 | 6.991 | 36.325 | 1.00 | 42.15 O |
| ATOM | 4888 | OH2 | WAT | 1258 | 22.019 | −1.420 | −22.953 | 1.00 | 31.72 O |
| ATOM | 5039 | OH2 | WAT | 1409 | 31.245 | 2.148 | 31.930 | 1.00 | 37.70 O |
| ATOM | 5051 | OH2 | WAT | 1421 | 27.033 | −0.096 | 31.578 | 1.00 | 53.89 O |
| ATOM END | | | | | | | | | |

What is claimed is:

1. An isolated heme/albumin complex having an atomic arrangement of coordinates comprising the coordinates as set forth in Appendix A.

2. A complex of hemalbumin having a crystal form of the space group C2 and unit cell dimensions of a=183.11 Å, b=37.91 Å, c=94.83 Å, and β=105.04°.

3. A complex of hemalbumin according to claim 2 wherein an active site comprises a hydrophobic surface of a binding pocket comprising amino acid residues Tyr-161, Phe-157, Arg-186, Leu-182, Arg-117, Phe-134, Leu-135, Leu-154, Phe-149, Ile-142, His-146, Arg-114, Lys-190, Ser-193, Ala-158, Tyr-138, Leu-115, Met-123, Phe-165, and Pro-118.

* * * * *